US008605981B2

(12) United States Patent
Rogan et al.

(10) Patent No.: US 8,605,981 B2
(45) Date of Patent: Dec. 10, 2013

(54) CENTROMERE DETECTOR AND METHOD FOR DETERMINING RADIATION EXPOSURE FROM CHROMOSOME ABNORMALITIES

(75) Inventors: Peter Keith Rogan, London (CA); Joan Helen Knoll, London (CA); Jagath Samarabandu, London (CA); Akila Subasinghe, London (CA)

(73) Assignee: Cytognomix Inc., London, Ontario (CA)

( * ) Notice: Subject to any disclaimer, the term of this patent is extended or adjusted under 35 U.S.C. 154(b) by 0 days.

(21) Appl. No.: 13/822,289

(22) PCT Filed: Nov. 4, 2011

(86) PCT No.: PCT/US2011/059257
§ 371 (c)(1),
(2), (4) Date: Apr. 18, 2013

(87) PCT Pub. No.: WO2012/061669
PCT Pub. Date: May 10, 2012

(65) Prior Publication Data
US 2013/0216118 A1    Aug. 22, 2013

Related U.S. Application Data

(60) Provisional application No. 61/410,849, filed on Nov. 5, 2010.

(51) Int. Cl.
*G06F 19/16*    (2011.01)
(52) U.S. Cl.
USPC .......................................................... 382/133
(58) Field of Classification Search
None
See application file for complete search history.

(56) References Cited

U.S. PATENT DOCUMENTS

| | | | |
|---|---|---|---|
| 4,122,518 | A | 10/1978 | Castleman et al. |
| 5,727,130 | A | 3/1998 | Hung |
| 5,751,908 | A | 5/1998 | Madau et al. |
| 6,132,961 | A | 10/2000 | Gray et al. |
| 6,347,308 | B2 | 2/2002 | Le Van Suu |
| 2006/0051739 | A1 | 3/2006 | Kanda |

OTHER PUBLICATIONS

Wang, Xingwei, A rule based computer scheme for centromere identification and polarity assignment of metaphase chromosomes, Computer Methods and Programs in Biomedicine; 89 (2008) p. 33-42.
Mousavi, et al; Feature Analysis and Centromere Segmentation of Human Chromosome Images Using an Interative, IEEE Transactions on Biomedical Engineering, vol. 49, No. 4, Apr. 2002 p. 363-371.

(Continued)

*Primary Examiner* — Stephen R Koziol
*Assistant Examiner* — Amandeep Saini
(74) *Attorney, Agent, or Firm* — Tracy Jong Law Firm; Tracy P. Jong

(57) ABSTRACT

A method for determining radiation exposure from chromosome abnormalities present in a specimen by determining the location or locations of the centromere of each chromosome in a cell in an image of a metaphase cell by segmentation of an accurately drawn chromosome centerline followed by selection of a longitudinal cross-section with the minimum width or intensity or width and intensity; counting the number of centromeres in each chromosome in each cell; computing the frequency of dicentric chromosomes in a population of cells; and determining the radiation dose by comparing the computed frequency of dicentric chromosomes with a previously determined dose-response curve from a calibrated source.

38 Claims, 8 Drawing Sheets

(56) References Cited

OTHER PUBLICATIONS

Subasinghe A, J Samarabandu, Knoll J, Khan W, Rogan PK. An Image Processing Algorithm for Accurate Extraction of the Centreline from Human Metaphase Chromosomes. 2010 IEEE International Conference on Image Processing, pp. 3613-3616. DOI: 10.1109/ICIP.2010.5652017.

Subasinghe A, J Samarabandu, Knoll J, Khan W, Rogan PK. An Accurate Image Processing Algorithm for Detecting Fish Probe Locations Relative to Chromosome Landmarks on DAPI Stained Metaphase Chromosome Images. IEEE 2010 Canadian Conference on Computer and Robot Vision. 2010. pp. 223-230. DOI: 10.1109/CRV.2010.36.

Arachchige, A.S.; Samarabandu, J.; Rogan, P.K.; Knoll, J.H.M. Intensity integrated Laplacian algorithm for human metaphase chromosome centromere detection. 2012 25th IEEE Canadian Conference on Electrical & Computer Engineering. pp. 1-4. DOI: 10.1109/CCECE.2012.6334866.

Li Y, A Wickramasinghe, A Subasinghe A, J Samarabandu, J Knoll, R Wilkins, F Flegal, and PK Rogan. Towards Large Scale Automated Interpretation of Cytogenetic Biodosimetry Data. Paper #1569626685. IEEE 6th Annual International conference on Automation for Sustainability, 2012. pp. 30-35 DOI: 10.1109/ ICIAFS.2012.6420039.

Subasinghe AA, J Samarabandu, J Knoll, PK Rogan. Intensity Integrated Laplacian Based Thickness Measurement for Detecting Human Metaphase Chromosome Centromere Location. IEEE Trans. Biomedical Engineering, Mar. 2013.

Ranjan R, A Subasinghe, J. Samarabandu, PK. Rogan, JHM Knoll. Automatic Detection of Pale Path and Overlaps in Chromosome Images Using Adaptive Search Technique and Re-Thresholding. Proceedings of International Conference on Computer Vision Theory and Applications, pp. 462-466, 2012.

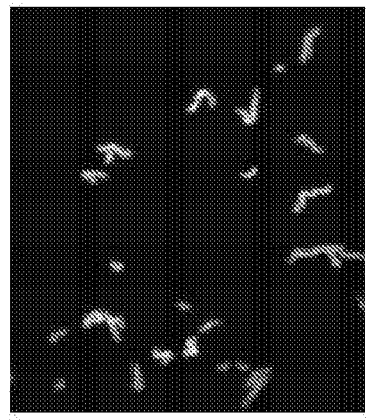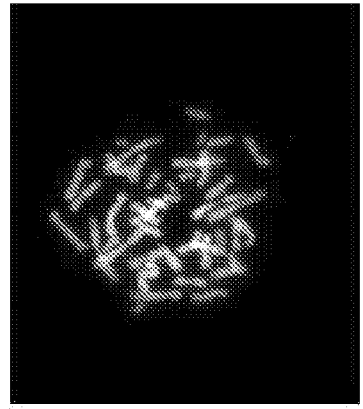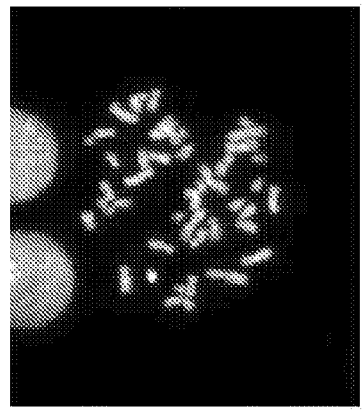
FIG. 1
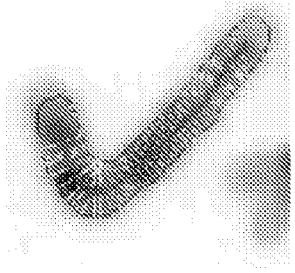
FIG. 2

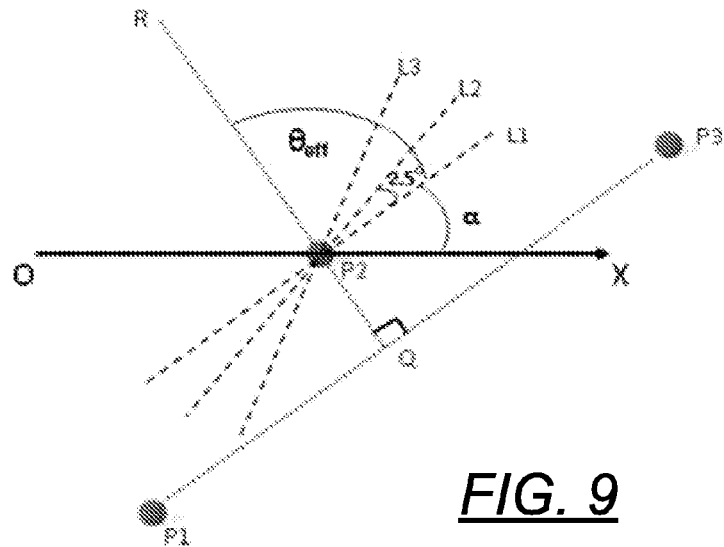
FIG. 9
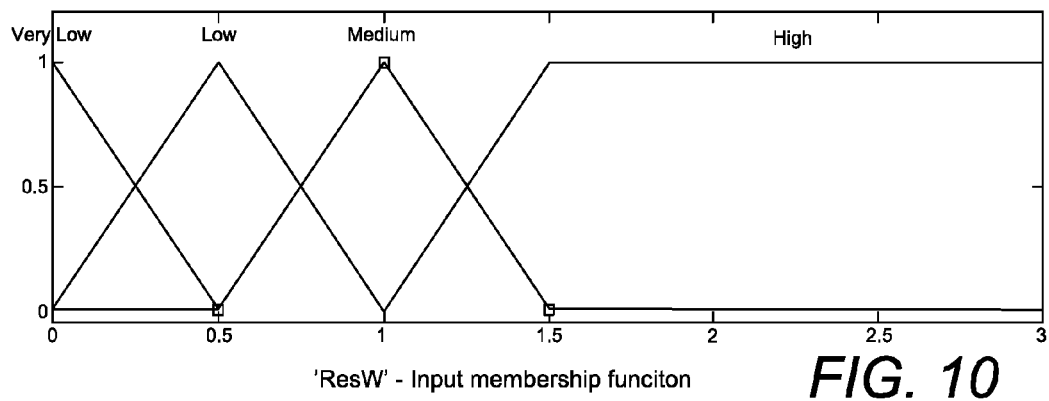
'ResW' - Input membership funciton   FIG. 10
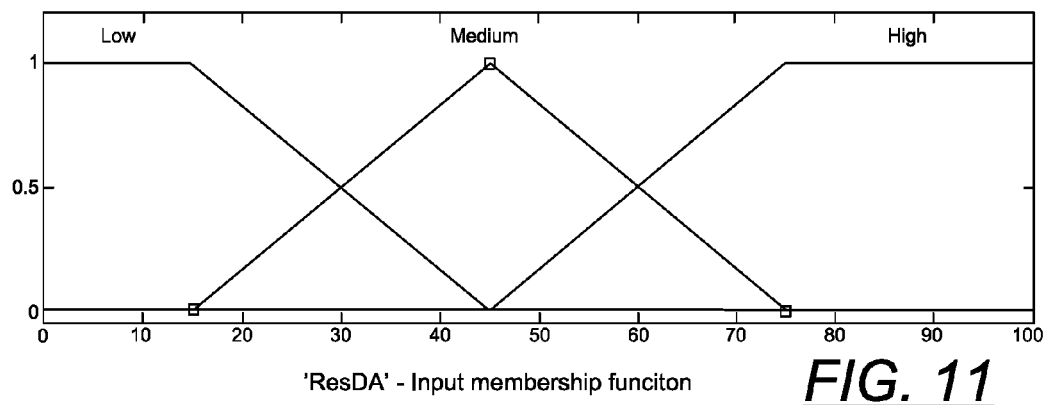
'ResDA' - Input membership funciton   FIG. 11

CENTROMERE DETECTOR AND METHOD FOR DETERMINING RADIATION EXPOSURE FROM CHROMOSOME ABNORMALITIES

PRIORITY AND RELATED APPLICATIONS

U.S. Ser. No. 61/410,849 filed Nov. 5, 2010; PCT/US2011/059257 filed Nov. 4, 2011.

BACKGROUND OF THE INVENTION

1. The Field of the Invention

The present method relates to determining radiation exposure, more specifically, to a method for analyzing chromosome damage in cells that have been exposed to ionizing radiation by analyzing images of their centromere.

2. Background Art

Chromosome testing of blood through microscopy and manual scoring are presently the gold standards for evaluating human radiation exposures. (Blakely W F, et al. *Health Phys.* 89:494-504, 2005). However, these techniques presented problems with obtaining an accurate throughput. In these well known methods, blood cell cultures are first analyzed by Giemsa or Bromodeoxyuridine/Hoechst 33258/Giemsa (Fluorescence plus Giemsa; FPG). This results in the staining of the chromosome during its metaphase stage. The stain spreads to determine the frequencies of the two most common forms of chromosome aberrations, dicentric chromosomes (DCC), and acentric chromosomes. The absorbed dose is subsequently determined by comparison with cellular standards exposed to calibrated radiation doses. This traditional method of recognizing dicentric chromosomes (DCC) currently involves microscopy and manual scoring by a cytogeneticist. However, these manual, non-automatic techniques severely limit the throughput of the DCC assay.

The accurate recognition of DCC must also be counterbalanced with the need to analyze thousands of metaphase images efficiently in the event of major radiation incidents or cases in which individuals are accidentally overexposed to medical or industrial radiation. Thus, automating this cytogenetic analysis has long been sought because of its impact on turnaround times following such unfortunate events.

There are commercially available semi-automatic cytogenetic systems. These systems basically depend on four features: (a) metaphase cell finding, (b) metaphase quality ranking, (c) relocation of metaphases at high magnification and (d) ability of systems to find analyzable metaphases otherwise overlooked by a cytogeneticist (Korthof G & A D Carothers. *Clin Genet.* 40(6):441-51, 1991).

A recent analysis with a commercial automated system produced rapidly collected scorable metaphase images. Unfortunately, this system showed 50% misclassification of the DCC (Vaurijoux et al. *Radiation Research* 171: 541-548, 2009). The reason for the high false detection was a faulty algorithm. The system used an algorithm that scored normal chromosomes as DCC when low radiation dose (<2 Gy) were present, especially in cells with underspread or overlapped chromosomes (Schunck et al. *Cytogenet Genome Res* 104: 383-389, 2004). Thus, there is a need for an approach which reduces false positive detection of DCCs arising from this category of metaphase cells.

Another problem with the present methods of analyzing chromosomes is that an imprecise method of image segmentation is used to partition the chromosome's metaphase image into many non-overlapping regions that correspond to individual chromosome objects. This causes error because chromosomes demonstrate high variability in shape on microscope slides mainly due to stages of cell cycle, length of mitotic arrest, slide preparation and banding patterns. This presents a significant challenge for automated segmentation, as well as for extracting the centerline of a chromosome, requiring expert input (Moradi M et al., "Automatic locating the centromere on human chromosome pictures," in *16th IEEE Symposium on Computer-Based Medical Systems*, 2003; Moradi M and S K Saterandan, *Pattern Recognition Letters*, 27:19-28, 2006).

Most existing approaches for chromosome segmentation rely on a form of pixel value thresholding (Graham J et al., *Chromosome Analysis Protocols*, 29:141-185, 1994). Thresholding is a point processing method that performs well on images consisting of objects well defined by pixel intensities that contrast clearly against background levels. Chromosomal images possess this quality to some extent. Otsu's method (and variations of this method) assign pixels as either object or background regions based on a single value, and have been used for the initial stage of segmentation of both Giemsa and DAPI banded (4',6-diamidino-2-phenylindole) chromosome images (Popescu M et al. *Computers in Biology and Medicine*, 29:61-82, 1999; Wolf G. et al., "*A PC-based program for evaluation of comparative genomic hybridization (cgh) experiments (URL)*"; Gajendran B and J. Rodriguez, in *Intl Conf on Image Processing (ICIP)*, pp. 24-27, 2004; Canny J, "A computational approach to edge detection," *IEEE Transactions on Pattern Analysis and Machine Intelligence (PAMI)*, 8(6), 1986; Ji, L. *Cytometry*, 17:196-208, 1994). Global thresholding by pre-processing images with a median filter, followed by 4-connected component labeling removes noise in the binary image (Wang X et al, *J Biomedical Informatics*, 41:264-271, 2008; Wang X et al., *J Biomedical Informatics*, vol. 42: 22-31, 2009).

Furthermore, all of these methods are prone to effects of uneven illumination, which can segment spurious objects that are partially discontinuous. The thresholded objects may contain holes due to small variations in illuminance (especially in fluorescence microscopy). Using local or adaptive thresholding, images have been divided into manually specified tessellations of fixed size and thresholded based on Otsu's method (Enrico G et al., in *Proc. 29th Intnl Conf of IEEE EMBS*, pp. 23-26, 2007; Otsu, N A. *IEEE Trans. on Systems, Man and Cybernetics*, SMC-9 (1): 62-66. 1979). Thresholded images are still sensitive to quantization errors present in the digital image. Intensity fading is also evident, resulting in cropping at the boundaries of the chromosome object.

Parametric deformable modeling has also been used to improve chromosome segmentation. Gradient Vector Flow (GVF)-based active contours is a modeling approach that exhibits greater accuracy for these objects. This model addresses a main limitation in the traditional active contours (Kass M et al., *Intnl J of Computer Vision*, 1(4): 321-331, 1988) by drastically increasing the capture range of contours (Xu C and J L Prince, "Gradient vector flow: A new external force for snakes," in *Proc IEEE Comp Soc Conf on Computer Vision and Pattern Recognition*, 1997).

The GVF snake model significantly improves chromosome segmentation compared to thresholding techniques (Britto P and G. Ravindran, *Inform Tech Journal*, 6 (1): 1-7, 2007; Li C et al, "Segmentation of edge preserving gradient vector flow: An approach towards automatically initializing and splitting of snakes," in *Proc IEEE Comp Soc Conf on Computer Vision and Pattern Recognition*, 2005). Being a parametric active contour, the global minimum (of an objective function) is not guaranteed unless the control points are initialized in the vicinity of the desired contour. Otherwise, the contour could converge to an unwanted local minimum such as a chromosomal band (which has a strong intensity gradient), on a non-chromosomal structure or even on the contour of another chromosome.

The chromosome's centerline is an important feature that serves as a reference for numerous measurements. The centerline feature is essential for recognition of centromeres and ultimately, DCC. It can be used to obtain the total length of the chromosome, the centromere location and centromere index value, the coordinates of the telomeric regions, and the banding pattern of a chromosome, all which may identify and classify a particular chromosome. Medial Axis Transform (MAT) and morphological thinning are often used to locate the medial axes of chromosomes. The boundary of the segmented chromosome image can be smoothed by morphological closing (dilation followed by the erosion operators) before applying MAT to skeletonize and obtain the centerline (Wolf G. et al., "*A PC-based program for evaluation of comparative genomic hybridization (cgh) experiments* (URL)").

Obtaining the chromosome's centerline was normally achieved by numerous methods that involved the mapping of the chromosome's skeleton. Spurious branches in a chromosome's skeleton occur and have to be corrected. Bifurcations in the skeleton towards the ends of the chromosome can be mitigated by deriving a line from the triangle formed by the two segments and the telomeric chromosome boundary (Moradi M and S K Saterandan, Pattern Recognition Letters, 27:19-28, 2006). This method fails if branches form at a distance from the telomere, which is common in bent chromosomes. Thinning procedures produce fewer spurious branches than skeletonization, however, the thinned result often has missing data at the chromosome ends (Lam L & S W Lee, *IEEE Trans on Pattern Analysis & Machine Intelligence*, 14:869-885, 1992; Jang B K and T C Roland, "Analysis of thinning algorithms using mathematical morphology," *IEEE Trans. on Pattern Analysis and Machine Intelligence (PAMI)*, 12(6), March 1990). Morphological thinning of binarized and median filtered chromosome images has been used to obtain the centerline (Gajendran B and J. Rodriguez, in *Intl Conf on Image Processing (ICIP)*, pp. 24-27, 2004; Wang X et al., *J Biomedical Informatics*, vol. 42: 22-31, 2009; Wang X. et al. *Comp. Meth. & Programs in BioMedicine*, 89:33-42, 2008). However, these approaches may still lead to spurious branches as well as bifurcations near telomeres. In images with rough chromosome boundaries, the spurious branches are prominent regardless of the filtering method. Subsequent pruning of these branches is the major limitation of both MAT and thinning. Furthermore, both procedures derive a set of points in space ("join the dots"), rather than a parametric curve, which is more relevant information for automated chromosome analysis. The medial axis has also been localized in straight chromosomes without skeletonization or thinning. Chromosomes are rotated until vertically oriented and midpoints of the horizontal chromosome slices are connected to obtain a medial axis which is then smoothed (Piper, J et al. *Cytometry*, 16: 7-16. 1994). Another method locates dominant points of the chromosome to derive a centerline[25]. Both approaches are not reliable if chromosomes are highly bent or blurred.

Sampling of chromosomes using cross-sections at different inclinations and combined midpoints can also be used to obtain an approximate medial axis (Ritter G and G. Schreib, *Pattern Recognition Journal*, 4: 923-938, 2001). However, the drawback of this method is that it attempts to get a polygonal approximation of the medial axis, instead of the medial axis itself and poor results were obtained when the segmented boundaries had irregular shapes. There is a need for a method for drawing the centerline accurately, and which is robust for various chromosome morphologies.

The chromosome's centerline is essential for recognition of centromeres and ultimately, DCC. For the foregoing reasons, there is a need for an automated method to determining radiation exposure, more specifically, to a method for analyzing chromosome damage in cells that have been exposed to ionizing radiation by analyzing images of their centromere.

SUMMARY OF THE INVENTION

To overcome the limitations of the prior art, there is provided a novel and previously unknown method for determining radiation exposure from chromosome abnormalities present in a specimen comprising the steps of:

(a) determining a location of at least one centromere of each chromosome in a cell in an image of a metaphase cell by:
  (i) segmenting an accurately drawn chromosome centerline for each chromosomes in the cell,
  (ii) selecting a longitudinal cross-section with a minimum width, intensity or combination of width and intensity,
  wherein in a dicentric chromosome, a location of a first centromere is masked to identify a subsequent longitudinal cross-section with a second lowest minimum width or intensity;
(b) counting the number of centromeres in each chromosome in each cell;
(c) computing the frequency of dicentric chromosomes in a population of cells; and
(d) determining the radiation dose by comparing the computed frequency of dicentric chromosomes with a previously determined dose-response curve from a calibrated source.

This novel process uses image segmentation methods that partition and identify optimal metaphase cells for automated analysis. The process also uses segmentation methods that correctly determine centromere location. Furthermore, fuzzy logic machine learning algorithms, which in this case are algorithms that allow computers to evolve behaviors based on empirical data from the images, are also utilized to identify DCC, acentric chromosomes, and monocentric chromosomes. This novel process also uses different chromosome staining procedures, such as DAPI and Giemsa staining, for optimal automated detection of DCC. Lastly, the process involves the creation of a software system to accurately identify DCC in optimally ranked metaphase spreads.

It is an object of the present invention to provide a process that analyzes chromosome abnormalities that are present in cells that have been exposed to ionizing radiation.

It is an object of the present invention to provide a process that avoids and/or minimizes false positive detection of dicentric chromosomes.

It is an object of the present invention to provide an automated process that accurately estimates human radiation exposures.

It is an object of the present invention to provide a process that automates aspects of the cytogenetic analysis.

Still another feature of this invention is that it improves centromere localization.

It is an object of the present invention to provide a process that utilizes image processing and machine learning approaches to discriminate DCCs.

These and other objects, features, and advantages of the present invention will become more fully apparent from the following description and appended claims, or may be learned by the practice of the invention as set forth hereinafter.

PARTICULAR ADVANTAGES OF THE INVENTION

The novel process avoids false positive detection by preselecting optimal metaphase spreads for analysis. Centromere localization is improved with DAPI and Giemsa staining methods that highlight centromeric regions that facilitate better discrimination of DCCs by image processing, allowing automation of the previously labor intensive and slow processes. In particular, heat denaturation of DAPI stained chromosomes can improve the accuracy of recognition of centromeres relative to Giemsa staining. The throughput and capabilities of the system can be expanded to determine DCC frequencies and compute radiation exposures in a cluster computer framework capable of managing data processing for a mass casualty event. The method for centerline determination performs well for short, long or highly bent chromosomes.

When combined with centromere detection, this novel process improves centromere detection. This is unobvious because the purposes for detecting centromeres are generally unrelated to ranking a collection of metaphase chromosomes in the same cell.

The novel process is capable of detecting irradiated chromosomes with significant sister chromatid separation. The novel process does not require straight chromosomes to accurately identify the centromere. The process has a lower false positive detection rate because the top ranked chromosomes are detected for analysis. It also has a higher sensitivity than commercially available automated processes and software such as that developed by another commercial cytogenetics microscopy imaging system, which detects only about 50% of dicentric chromosomes. In contrast, the present process detects 70-85% of dicentric chromosomes.

The novel process can be used to determine levels of exposure to ionizing radiation. Exposure doses estimated from dicentric frequencies are used to make treatment decisions in mass casualty and industrial exposures to ionizing radiation. This novel process can also be used to accurately determine the dose of whole body exposure to ionizing radiation through the analysis of dicentric chromosomes in blood. The novel process provides an accurate and efficient automated method of determining dicentric chromosome frequency in blood.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIGS. 1A, 1B and 1C depicts results rankings where FIG. 1A is a nice image that is non-overlapped and non-overspread, FIG. 1B is an overlapped image, and FIG. 1C is an overspread image.

FIG. 2 depicts trellis structure and GVF result outline.

FIG. 9 depicts the setup of line sampling (L1, L2, L3 . . . ) for an interior centerline point P2.

FIG. 10 depicts 'ResW' input membership function.

FIG. 11 depicts 'ResDA' input membership function and the shape and parameter information of the output fuzzy membership function.

DETAILED DESCRIPTION OF A PREFERRED EMBODIMENT

Figure 3:
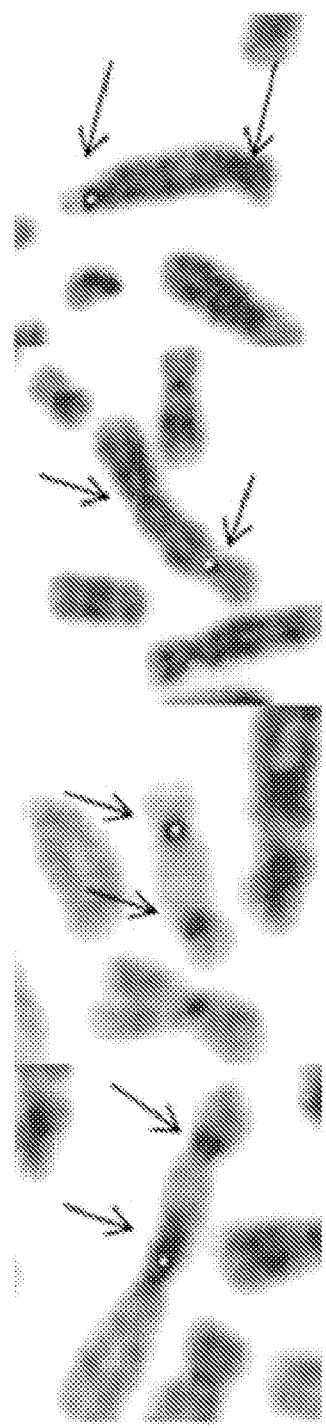
FIG. 3 depicts centromere detection (dots and arrows) by algorithm with DAPI stain.

Briefly, a method for determining radiation exposure from chromosome abnormalities present in a specimen comprises four sequential steps: (a) determining a location of at least one centromere of each chromosome in a cell in an image of a metaphase cell by segmenting an accurately drawn chromosome centerline of each of the chromosomes in the cell and selecting a longitudinal cross-section with a minimum width, intensity or combination of width and intensity; (b) counting the number of centromeres in each chromosome in each cell; (c) computing the frequency of dicentric chromosomes in a population of cells; and (d) determining the radiation dose by comparing the computed frequency of dicentric chromosomes with a previously determined dose-response curve from a calibrated source. In the case of a dicentric chromosome, a location of a first centromere is masked to identify a subsequent longitudinal cross-section with a second lowest minimum width or intensity. Each of these steps is described in greater detail below.

As used in this specification, complete chromosome number shall typically mean 46 chromosomes in humans, except when abnormalities are present which increase or decrease this number by one or a few chromosomes.

As used in this specification, degree of overlap shall mean the number of chromosomes in which a portion of a chromosome lies either on top of or below another chromosome. As used in this specification, centromere confidence value shall mean a percentile value which depicts the probable accuracy of the centromere detection method for each chromosome.

As used in this specification, standard deviation of the area shall mean the standard deviation of the area value of all detected object area values.

As used in this specification, aspect ratio shall mean the ratio between the width of the image and the height.

As used in this specification, total area shall mean the total pixel area of the objects. This value can be a simple pixel count of the area.

As used in this specification, ratio of severe overlap shall mean the ratio of overlapping objects to that of the total number of objects.

As used in this specification, brightness shall mean the luminance of the object of interest or the image and is directly represented by the pixel intensities.

As used in this specification, contrast shall mean the difference of image intensity levels between the object and the background.

Pre-Selection of Optimal Metaphase Chromosome Images

Pre-selection of optimal metaphase chromosome images significantly reduces false positive identification of DCC, which has been noted in previous attempts to automate their detection. The pre-selection procedure minimizes analysis of cells with many overlapping chromosomes and images of overspread cells with an incomplete set of chromosomes. Detection of normal (and abnormal) chromosomes is facilitated in metaphase cells with few overlapped or overspread chromosomes. Similar metaphase qualification procedures are routine in biodosimetry studies performed by routine manual interpretation. We previously developed an automated system to select optimal metaphase cells for such cytogenetic analyses (Yanala et al. Am Soc. Human Genet. Ann. Meeting, 2004).

Our automated system ranked metaphase spreads using a content and classification-based ranking (CCBR) algorithm which emphasized relationships between features extracted from metaphase chromosomes (Kobayashi T et al. "Content and classication based ranking algorithm for metaphase chromosome images," *IEEE Conference on Multimedia Imaging and Expo.*, June 2004). The CCBR is derived from cytogeneticist-defined quality metrics and ranks images according to those specialist criteria.

Images are categorized as either "nice", "overlapped" or "overspread" and then subclassified. Nice images are assigned the highest ranks, followed by overlapped and overspread chromosomes. Overspread images are likely to have incomplete karyotypes. 17 different features are extracted using morphological image processing tools (Serra J P, Image Analysis and Mathematical Morphology. *New York: Academic*, 1982; Haralick, R M et al *IEEE Trans. System, Man, Cybernetics* 3:610-621, 1973). Examples of ranked images are depicted in FIG. 1.

In CCBR, we define E as a chromosome entity. If a chromosome doesn't overlap others, E is the chromosome itself; if a chromosome does overlap, E is the chromosome connected to neighboring chromosomes. We define each image I as the set of all E's in a cell. Features extracted from each image included average and standard deviation of the area, length, perimeter, aspect ratio, and parwise distance of all E's. Global features include total area of E's, E count, image density (size of smallest rectangle containing all E's) and ratio of severe overlaps (the ratio of the number of overlapping E's to the E count), and brightness/contrast (proportion of pixels with gray scale<0.1) of all E's.

Nine of these features were sufficient to classify the image into one of the categories. The nice image standard feature vector is the mean value of all nice image feature vectors in the database of training images.

Once the images are classified, they are ranked within a category based on total area, ratio of severe overlaps, mean pair-wise distance and brightness & contrast. Within the nice and overlapped categories, images with severe overlaps or fuzziness are assigned lower ranks. The local rank of an image within the nice or overlapped category is based on the total area of E's, the ratio of severe overlaps, and brightness & contrast. The local rank of images in the overspread category is determined by the total E count, the mean and standard deviation of their pair-wise distances. Images with more chromosome entities and smaller average distance of pair-wise chromosomes are ranked highly.

This automated metaphase ranking method has an average precision of 88.8% [true pos/(true pos+false pos)] with an 80% recall [true pos/(true pos+false neg)] rate relative to ranking by an experienced cytogeneticist (Yanala P et al. *Am Soc. Hum Genet Ann. Conf.*, Program No. 997, 2004) based on 443 images captured from 8 different microscope slides. The top 25% ranked images and bottom 15% ranked images were examined further. The results showed the top 30 ranked images on each slide were devoid of false positives. Of the 265 images ranked in the top 25%, 19 were misclassified as nice images. Most of these misclassifications were from nuclei in late interphase being interpreted as metaphase cells. They can be excluded by detection of the curvature of the nuclear membrane which is intact in these cells. Of the 179 bottom ranked images, 23 are misclassified as poor, even though they possessed a complete set of non-overlapping chromosomes. Micronuclei present in these same images are incorrectly classified as overlapped chromosomes, which lower the rank. These structures will be identified and masked in the next version of the algorithm.

TABLE

| Ranking results for DAPI-stained metaphase cells at 100x magnification | | | | | | |
|---|---|---|---|---|---|---|
| Slide ID | No. of Images | No. of Metaphases (true positives) | No. of False Positives | % False Positive Objects | False Positive images in top 50 ranked images | False Positive images in top 30 ranked images | Identification/Remarks on False Positive Objects |
| 3041 | 468 | 390 | 78 | 16% | 0 | 0 | Small nuclei clusters, debris, non-centered metaphases + small nuclei |
| 3068 | 93 | 78 | 15 | 16% | 0 | 0 | Bright nucleoli, non-centered metaphases + nuclei |
| 2947 | 115 | 99 | 16 | 13% | 5 | 0 | Debris, bright nucleoli, small nuclei clusters, prometaphase cells |
| 3039 | 119 | 107 | 12 | 10% | 1 | 0 | Debris, antifade mounting artifact |
| 2951 | 142 | 96 | 46 | 32% | 1 | 0 | Overall pale DAPI staining, bright nucleoli, prometaphase cells |

TABLE-continued

Ranking results for DAPI-stained metaphase cells at 100x magnification

| Slide ID | No. of Images | No. of Metaphases (true positives) | No. of False Positives | % False Positive Objects | False Positive images in top 50 ranked images | False Positive images in top 30 ranked images | Identification/Remarks on False Positive Objects |
|---|---|---|---|---|---|---|---|
| 3473 | 104 | 99 | 5 | 4% | 0 | 0 | More dilute cell preparation with nuclei of uniform size; fewer false positives |
| 3017 | 524* | 467 | 57 | 11% | Not Ranked | Not Ranked | Debris, clusters of small nuclei |
| 3468 | 77** | 63 | 14 | 18% | Not Ranked | Not Ranked | Out of focus nuclei and chromosomes***, concentrated cell preparation, thick antifade |

Defining Chromosome Features and Centerline Determination

Our premise is that the recognition of DCC depends on precise and accurate centromere localization. The centromere is the most condensed and constricted region of a chromosome, to which the spindle fiber is attached during mitosis (cell division) (Wang X. et al. Comp. Methods and Programs in Bio Medicine, 89: 33-42, 2008). This constriction is not always obvious, especially in bent chromosomes. The difficulty in identifying centromeres depends on their location, chromosome length, and variability in chromosome morphology. The medial axis of the chromosome embodies these properties, and it is a critical prerequisite for correct centromere assignment. We have developed a novel method for centerline determination. Our work differs from the previously discussed approaches in that it performs well for short, long or highly bent chromosomes.

To derive the centerline of a chromosome, it is necessary to first define its contours precisely. Fluorescent metaphase images of DAPI-stained chromosomes were pre-processed for chromosome segmentation. Following gray scale conversion, variations in lighting across an image were alleviated by extracting a rectangular shaped window that included the chromosome and adjacent background. Intensities were then normalized by window center adjustment and mapped across the complete spectrum of possible pixel values. A simple threshold was applied based on Otsu's method (which creates a binary image). Because binary images generated by fluorescence microscopy produce irregularities (Kozubek M, Image Acquisition and its Automation in Fluorescence Microscopy. Springer Netherlands, V3, 2006), the threshold result was used only for pre-segmentation. The images were subjected to our ranking algorithm (Kobayashi T et al. "Content and classification based ranking algorithm for metaphase chromosome images," IEEE Conference on Multimedia Imaging and Expo., June 2004), which selects optimal chromosomes and improved overall accuracy of subsequent processing steps. A scaling factor was applied to the thresholded image, imposing under-segmentation on higher ranked images and reducing the possibility of getting a cluster of chromosomes as the segmentation result.

The complement of the DAPI stained image is commonly used to illustrate a wide range of image intensity information like chromosome banding patterns. After eliminating shot noise (blobs<10 pixels), the chromosome was extracted from the binary image by connected component labeling of a 4-connected graph. This removed discontinuities present within and at the boundary of the object. The initial chromosome contour was traced using a 3×3 neighborhood (Image Processing Toolbox (URL)) which retained boundary information. Then, an active contour (or snake) was applied to determine the chromosome outline. The snake iteratively converges towards the closest local minima of image gradients from an initial set of control points. Bends in metaphase chromosomes can create concave boundaries which prevent convergence of conventional snakes. The capture range of the snake can be increased by smoothing the boundary map of an image with a Gaussian kernel (GVF-active contour) (Xu C and J L Prince, "Gradient vector flow: A new external force for snakes," in Proc IEEE Comp Soc Conf on Computer Vision and Pattern Recognition, 1997). Iterating the GVF-contouring procedure resulted in chromosome defined boundaries that were accurately detected (Canny J, "A computational approach to edge detection," IEEE Transactions on Pattern Analysis and Machine Intelligence (PAMI), 8(6), 1986).

Centerline Detection.

The centerline of an object is the set of all points which are centers of circles that touch the image surface at more than one point (Blum H, in Models for the Perception of Speech and Visual Form, pp. 362-380, MIT 1967). The centerline of a chromosome represents skeletal shape and topological information present in the original chromosome. Accurate detection of the chromosome centerline is a critical operation in many karyotyping algorithms (Popescu M et al. Computers in Biology and Medicine, 29:61-82, 1999; Piper, J et al. Cytometry, 16: 7-16. 1994; Ritter G and G. Schreib, Pattern Recognition Journal, 4: 923-938, 2001; Kao J H et al, The Journal of Pattern Recognition Society, 41:77-89, 2008). Morphological thinning or skeletonization is commonly used to extract the centerline, but the variability of metaphase chromosomes introduces errors. Spurious branches present in the skeleton have to be pruned, either during derivation of the skeleton or post-processing. We adopted a pruning method based on Discrete Curve Evolution (DCE) (Latecki L J and R. Lakamper, Comp Vision and Image Understanding, 73: 441-454, 1999; Bai X et al. IEEE Trans. on Pattern Analysis and Machine Intelligence (PAMI), 29(3), 2007), which models the skeleton as a polygon with a specified number of vertices. DCE pruning was applied to chromosomes with skeletons longer than 35 skeletal points; shorter, straight chromosomes were processed by conventional thinning (Lam L & S W Lee, IEEE Trans on Pattern Analysis & Machine Intelligence, 14:869-885, 1992). DCE contours were partitioned into polygonal sections, then pruned by removing all skeletal points which generated points on the same polygonal partition. Since the minimum polygon is a triangle, the resulting skeleton will have a single spurious branch. DCE deletes vertices without moving them. There is no dislocation of feature points and or dislocation of the skeleton (Bai X et al.

*IEEE Trans. on Pattern Analysis and Machine Intelligence (PAMI)*, 29(3), 2007; Latecki L J and R. Lakamper, in *Proc of 2$^{nd}$ Intl Conf on Scale-Space Theories in Computer Vision*. pp. 398-409, 1999). This method provides a good starting point for identifying the true longitudinal axis of the chromosome.

Although thinning or skeletonizing algorithms generate a connected, one-pixel thick skeleton (Jang B K and T C Roland, "Analysis of thinning algorithms using mathematical morphology," *IEEE Trans. on Pattern Analysis and Machine Intelligence (PAMI)*, 12(6), March 1990), this is not guaranteed. The DCE-pruned skeleton was processed using a modified thinning operation that applied "morphological hit & miss" masking, followed by subtraction of the result from the binary skeleton image. Pruning the shortest skeletal branch was found to produce the correct centerline for skeletons of chromosomes of various shapes and lengths. A curve fitting step (cubic spline interpolation fitting a third order polynomial) was then used to obtain a smooth continuous curve from the skeleton. Control points were sampled from the pruned skeleton to prevent overfitting, while representing the fundamental shape information adequately. Based on expert assessment, DCE based method outperformed conventional thinning for 20 of 68 chromosomes tested, and they were equivalent for the rest (Subasinghe A. et al. "An image processing algorithm for accurate extraction of the centerline from human metaphase chromosomes. *IEEE International Conference on Image Processing*, 2010, in press).

Centromere Detection.

We recently published (annexed hereto) a novel algorithm for accurately tracing the medial axis of chromosomes, and identifying the centromere and telomeres, and have demonstrated that DNA probe distance measurements relative to these chromosome features are determinable (Subasinghe A et al. *Canadian Conf. on Computer & Robot Vision*, pp 223-230, DOI: 10.1109/CRV.2010.36, 2010). The end-pruned centerline is used as the reference to determine centromere location. Selection of the reference line segment drastically simplified the centromere detection process, as it excludes the extreme ends of the chromosome. Trellis line segments were drawn perpendicular to the pruned centerline segment at unit length intervals. The cross sectional width is the length of a trellis line segment. The sample intensities along the trellis were weighted with a Gaussian function which was intended to cancel image and boundary noise as well as undesirable effects introduced by chromosome bending. Though the sampling of intensities along the trellis was performed on the filtered DAPI image, the lengths of the trellis segments were decided from the binary result obtained through the GVF. Use of the GVF result based on the binary image has better defined edge characteristics than a simple thresholded binary image, which makes the constriction at the centromere more pronounced. The centromere was located using the width profile (Wp) of the chromosome along the trellis on the medial axis of the GVF binary image and the intensity profile (Ip) obtained by getting the weighted average of intensity values of the DAPI image (based on a Gaussian function) along the GVF-limited trellis.

Applicant uses a novel approach termed 'Intensity integrated Laplacian thickness measurement' for obtaining the thickness/width profile of human metaphase chromosomes. The Laplacian operator ($\Delta$) yields the divergence of the gradient of a function in the Euclidian point space. In other words, it gives the difference of the gradient or the first order derivative of a function or an image. This can be written as follows, where $\nabla$ is the first derivative or the differential operator in any given direction.

$$\Delta f = \text{div}(\nabla f) = \nabla \cdot \nabla f$$

When applied to an image, the Laplacian operator yields the second order derivative of the image which emphasizes the edge or contour information. This operator can also be used to obtain the steady state of heat flow or voltage distribution between two heated/charged surfaces.

The thickness measurement process proposed in this work utilizes the following information obtained in earlier stages,
1. The single pixel wide contour of the segmented object of interest. The contour should comprise of coordinate locations sorted based on connectivity.
2. Separation of the object contour using the centerline of the object. This can be derived by calculating the coordinates of the intersecting points between the centerline and the object contour.
3. The extracted object of the chromosome which contains the intensity information within the object.

Let 'I' be the intensity image which contains the object of interest. Then we can create a second image 'B' of identical dimensions and set one contour line segment at a potential of 1 volt while keeping the other at ground potential (0 volt). Then by definition the Laplacian of image 'B' can be represented using equation, $$\Delta B = \frac{\partial^2 B}{\partial x^2} + \frac{\partial^2 B}{\partial y^2}$$

Figure 7:
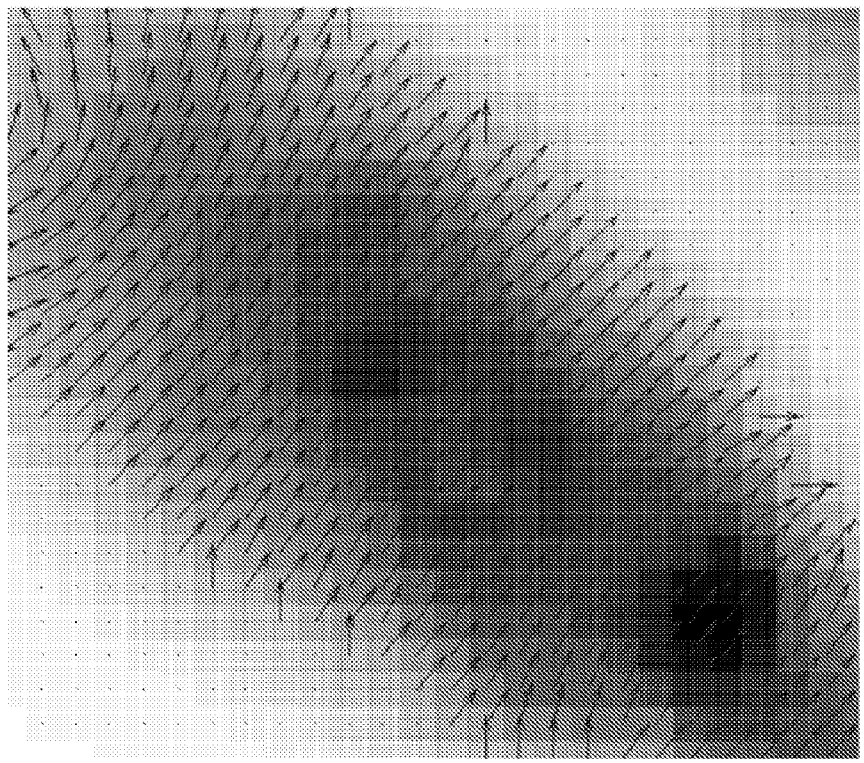
FIG. 7 depicts such a static vector field calculated at the steady state using the Laplacian equation.

The application of the standard Laplacian equation on image 'B' results in the voltage of the higher potential contour line segment getting dispersed across the object body onto the lower potential contour line. Here, the higher potential values will spread through the object body towards the lower potential line segment while gradually decreasing magnitude. At steady state, these potential values can be used to create a static vector field that can be used for traversing from one contour partition to the next in the shortest possible distance. FIG. 7 depicts such a static vector field calculated at the steady state using the Laplacian equation. Referring to FIG. 7, the static vector field (arrows) calculated by applying the Laplacian equation to the chromosome boundary information. The arrows signify the direction of the gradient of the system at steady state.

The process of calculating the steady state potential values can be modeled easily as an iterative process in the digital domain. Using a 3×3 neighborhood, the iterative Laplacian operation equation for pixel coordinates (x, y) at the instance i+1 can be given by the following equation, $$B_{i+1}(x, y) = \frac{9}{8} B_i(x, y) - \sum_{i=-1}^{i=+1} \sum_{j=-1}^{j=+1} \frac{B_i(x+i, y+j)}{8}$$

Yet, the above implementation would solely depend on the boundary contour information. Segmenting an object is a process highly influenced by noise present around the boundary of the object. Therefore, a noisy object contour would yield an undesirable thickness/width profile. Intensity information can be utilized to assist thickness measurements of textured objects in chromosome images. Most of these intensity patterns provide information regarding the direction which the thickness measurement lines should propagate. Therefore, applicants use an algorithm for incorporating intensity information in to the standard Laplacian static vector filed calculation. The intensity information in the proposed method was simply used to bias the field towards the desired intensity pattern. This was achieved by using the weighting scheme described below.

Image Intensity Integration

Image intensities typically are used to segment an image into regions or to find edge-fragments by using the concept of light flux per unit area. In this novel process, image intensity is utilized along with the Laplacian thickness measurement formula to detect the contours of the chromosome.

First, a total of 8 matrices were created based on connectivity and directional intensity gradients with identical dimensions to 'I' as follows, $$D_{up}(x,y)=abs[I(x,y)-I(x,y-1)]$$

$$D_{dw}(x,y)=abs[I(x,y)-I(x,y+1)]$$

$$D_{lf}(x,y)=abs[I(x,y)-I(x-1,y)]$$

$$D_{rt}(x,y)=abs[I(x,y)-I(x+1,y)]$$

$$D_{lu}(x,y)=abs[I(x,y)-I(x-1,y-1)]$$

$$D_{ru}(x,y)=abs[I(x,y)-I(x+1,y-1)]$$

$$D_{lb}(x,y)=abs[I(x,y)-I(x-1,y+1)]$$

$$D_{rb}(x,y)=abs[I(x,y)-I(x+1,y+1)]$$

Each of the above matrices captures the intensity variation in a pre-specified direction in the digital image. For simplicity and clarity, the rest of the steps will be described using only one of the above 8 images ($D_{up}$). Next, all the images were normalized using the maximum absolute intensity difference in that direction using the following equation.

$$D_{up} = \frac{D_{up}}{\max(D_{up})}$$

Therefore the values in the matrix '$D_{up}$' will be normalized to the interval (0, 1). Since chromosomes demonstrate similar intensity regions normal to the contour, the weighting scheme should bias towards similar intensities. To achieve this, the matrix values were inverted within the same range of (0, 1) by subtracting each matrix value from the value unity. The matrix '$D_{up}$' will now yield values close to unity where intensity level in the neighborhood is similar. Similarly, the matrices will also yield smaller values (close to 0) for pixels with high intensity gradients in the neighborhood. By doing so, the algorithm will encourage the dispersion of the potential values in the direction of the intensity similarity. Since the intensity information had to be used only as a biasing factor, each of these matrices (say $D_{up}$) were rescaled using a variable 'b' as given below, $$D_{up}=D_{up}\times(1-b)+b$$

A lower value for 'b' will increase the influence of the intensity information and vice versa. Therefore, a value of '1.0' for the variable 'b' will calculate the standard Laplacian vector field with no influence from the intensity values. This value has to be set based on how prominent and consistent the intensity patterns are in a given image. For this application, the value of the scaling variable 'b' was set to 0.9.

Once these sets of intensity weighting factor matrices are calculated, those values can be directly used to change the way the Laplacian static field is calculated at each iteration. Unlike the standard Laplacian field calculation, the contribution from neighborhood pixels will vary from pixel to pixel.

The voltage or heat values in the neighborhood of the pixel (x, y) will be weighed according to the following equation, $$B_{i+1}(x, y) = \begin{matrix} B_i(x, y) \\ -(1/8)\times D_{up}(x, y)\times B_i(x, y-1) \\ -(1/8)\times D_{dw}(x, y)\times B_i(x, y+1) \\ -(1/8)\times D_{lf}(x, y)\times B_i(x-1, y) \\ -(1/8)\times D_{rt}(x, y)\times B_i(x+1, y) \\ -(1/8)\times D_{lu}(x, y)\times B_i(x-1, y-1) \\ -(1/8)\times D_{ru}(x, y)\times B_i(x+1, y-1) \\ -(1/8)\times D_{lb}(x, y)\times B_i(x-1, y+1) \\ -(1/8)\times D_{rb}(x, y)\times B_i(x+1, y+1) \end{matrix}$$

The convergence or the steady state of the above iterative process can be measured using the cumulative variation of values in the static vector filed. If the cumulative change in the vector field for the image is lower than a small threshold value ($1\times10^{-10}$ in this experiments), the iterative process is terminated and the steady state is achieved. Once in the steady state, the gradients at each pixel location 'ϕ' was calculated along the two major axes (x and y) using neighborhood pixel values as given below, $$\frac{\Phi(x, y)}{\Delta x} = \frac{(B(x+\Delta x, y) - B(x+\Delta x, y))}{2\Delta x}$$

$$\frac{\Phi(x, y)}{\Delta x} = \frac{(B(x, y+\Delta y) - B(x, y-\Delta y))}{2\Delta y}$$

Each of these gradient components were then normalized and stored in matrices $N_x$ and $N_y$ using the magnitude of the vector at each pixel. The matrices $N_x$ and $N_y$ contain the intensity biased Laplacian static field vector components for x and y axis directions.

Once the proposed intensity integrated Laplacian static field is derived, the corresponding contour points and the distance between them have to be calculated. Euler's method was used for the above task. Euler's method is a simple and yet effective way of traversing through a vector field as given by the following equation based on the local vector field direction and magnitude.

$$\bar{x}=x+\Delta x$$

$$\bar{y}=y+y'\cdot\Delta x$$

Here y' is the first derivative at that location which is given by $N_y(x,y)/N_x(x,y)$.

Figure 8:
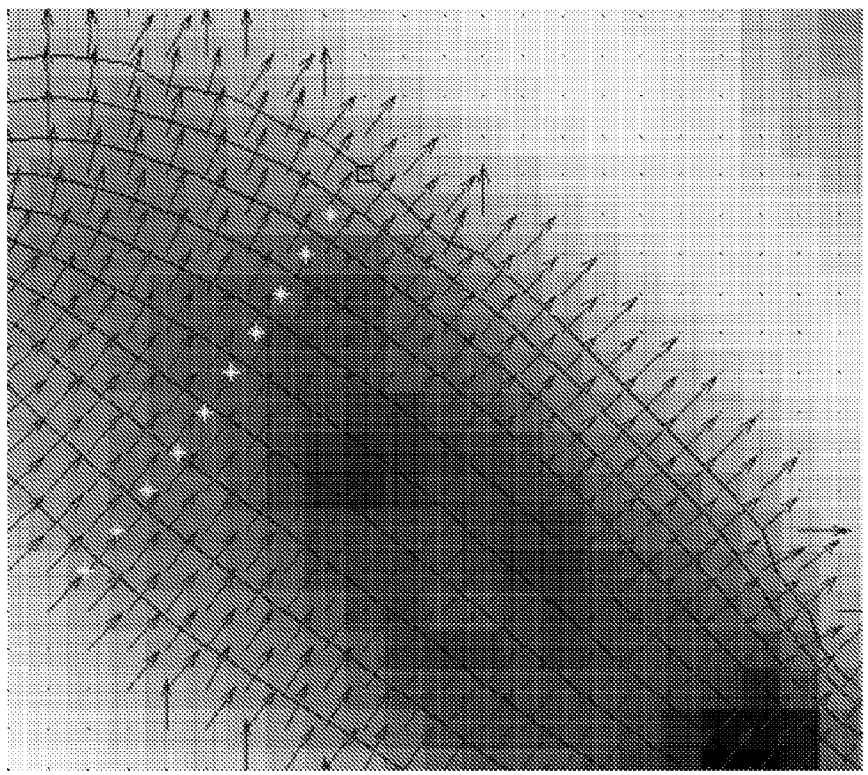
FIG. 8 depicts the steps of tracing the thickness at one contour location of the chromosome.

FIG. 8 depicts the steps of tracing the thickness at one contour location of the chromosome. Once the thickness and intensity measures starting from selected points on one side of the object contour are calculated, we select the global minimum of the combined profile as the candidate location for the centromere. The selection of contour points was set up at 80% of the total length of the contour to avoid measuring the thickness values at the telomeric regions. Referring to FIG. 8, the steps of tracing the thickness (stars) at one contour location of the chromosome. The final thickness value is calculated by getting the sum of all the lengths of these small steps.

We developed a 'centromere confidence value' (CCF) to measure the probable accuracy of the automated centromere detection process. CCF is expressed as a percentage which approximates the degree of confidence of the detected location. CCF is based on Wp(i) and Ip(i), the respective width and intensity profiles of centerline points i=1, 2 ... N of a chromosome. Sp is the global minimum (selected as centromere) of the combined profile. Then, the values $W_m$ and $I_m$ are defined as the minimum values in Wp(i) and Ip(i). The vector, Vwp, that contains all the centerline points with the minimum width value is: Vwp={u∈Wp(i)|Wp(i)=$W_m$, ∀i=1, 2 ... N}. The value $Wid_{Wp}$ is calculated as the cardinality of Vwp. We define:

$$CCF = \frac{W_m + I_m}{S_p \times F_c} \times 100\% \text{ where } F_c = \begin{cases} 0.55 \times Wid_{Wp}, & \text{if } Wid_{Wp} > 1 \\ 1, & \text{if } Wid_{Wp} = 1 \end{cases}.$$

CCF is high if the sum of the minimum of the width and intensity profiles are equal or closer to the selected combined minimum point (centromere). If the trellis segments miss the true centromeric constriction due to extreme bends or perturbations in the centerline, the width profile may contain multiple points with a global minimum value ($Wid_{Wp}$>1). The $F_c$ term reduces CCF in the presence of multiple global minima. Of 41 normal chromosomes, the centromere was assigned accurately in 25 cases, it was slightly off-center in 12 but localized within the correct chromosome band, and 4 were incorrect (10%). The CCF measure will be further improved in the future. One approach is to add a margin (+/−) % value of the minimum width, in considering the vector Vwp.

This previously developed algorithm only concerned ranking of metaphase images. There was no motivation to analyze centromeres. At the time of filing this provisional application, Applicants have compared denatured and non-denatured DAPI stained chromosomes and have collected data showing that centromere staining is feasible with other methods such as C Banding, CENPB immunostaining and centromeric FISH.

Automated recognition of dicentric (and acentric) chromosomes is maximized with the best possible accuracy by coordinated evaluation of chromosome staining methods and companion imaging techniques. Biodosimetry samples/data are used for refinement of segmentation methods for distinguishing optimal chromosome images. We analyze images by segmentation, and machine learning approaches to accurately distinguish monocentric, dicentric and acentric chromosomes. We then evaluate and select chromosome staining methods that improve automated detection of these chromosome abnormalities. The best performing methods are codified in a software system to rank, analyze and manage metaphase chromosome image data from automated microscopy systems and determine DCC frequencies.

Software automatically ranks and interprets images of metaphase chromosomes (Wang X et al., *J Biomedical Informatics*, vol. 42: 22-31, 2009) and detects abnormal DCC. The automated microscopy system locates the optimal metaphase cells for analysis and subsequently those containing DCC and determines their frequencies. The algorithms we have developed for detecting the centromere of a chromosome image primarily use two visual cues: constrictions and staining intensity. We initially determine the distribution of CCF values for metaphases captured by our microscope system for each sample for each method of preparing/staining chromosomes to assess the reliability of current algorithms. Applicants have done this for mono and dicentric chromosomes. The acentric fragments can be detected with the CCF equation and one skilled in the art applying this formula would expect that it would distinguish acentric from mono and dicentric fragments.

While this method is a good starting point for detecting DCC, it needs additional processing algorithms to obtain better performance. The final algorithm contains the following steps: (1) Cell ranking and detection of chromosome overlap and sister chromatid separation; (2) Generation of candidate locations of centromeres and of acentric fragments (3) Refinement of candidate locations.

Selecting Optimal Metaphase Chromosome Spreads for Automated Analysis.

To select optimal images of irradiated chromosomes, images captured by the microscope system are rank ordered based on chromosome spreading, sharpness and the degree of overlap. The current algorithm, which ranks FISH images based on content classification (Kobayashi T et al. "Content and classification based ranking algorithm for metaphase chromosome images," *IEEE Conference on Multimedia Imaging and Expo.*, June 2004), is modified to exclude and mask clusters of micronuclei that are sometimes misinterpreted as metaphase spreads. Additional measures can be implemented to address some unique aspects and requirements of irradiated chromosomes.

Accurate biodosimetry requires cells that have undergone only a single mitotic division post-irradiation because the frequency of DCC can be diluted in subsequent divisions. Cells that have completed a single mitotic division have both chromatids homogenously stained by the FPG technique (and FPG followed by DAPI staining). Cells undergoing multiple divisions exhibit chromatids with variable staining.

The cross-sections of highly ranked metaphase images are further analyzed to eliminate those in which sister chromatids of the same chromosome are non-homogenous. In addition, we also implement published algorithms that will allow us to separate overlapped and adjacent chromosomes (Agam G & Dinstein I. *IEEE Transactions on Pattern Analysis and Machine Intelligence*, 19(11): 1212-1222, 1997; Grisan E et al. *IEEE Transactions on Information Technology in Biomedicine*, 13(4): 575-581, 2009). The curvature of the chromosome contour is analyzed to identify points where chromosomes intersect, and to connect these points at the overlap junctions. We investigate the performance of these algorithms and implement a suitable algorithm that allows us to identify overlapped chromosomes and separation of sister chromatids. The latter is of particular importance as it tends to significantly change the shape of the chromosome. We also specify acceptance criteria based on all these measures which are used to select images that are then processed in the subsequent steps.

Determining Centromere Locations; Machine Learning to Distinguish Chromosomes with Different Numbers of Centromeres.

We generate candidate positions for centromeres, minimizing false-negative detection at the expense of increased false-positives. Our starting point is the process that was developed for detecting centromeres in FISH images (Subasinghe A et al. *Canadian Conf. on Computer & Robot Vision*, pp 223-230, DOI: 10.1109/CRV.2010.36, 2010). Using calibrated biodosimetry data, the performance of this algorithm for images obtained with different cell staining and imaging conditions is compared with assessment by a cytogeneticist.

Once the centromere candidates are located, algorithms based on feature selection can be used to test the hypothesis that an object is a DCC. Visual cues used by cytogeneticists to detect DCCs in a cell image include the number and degree of constrictions, intensity variations (if any), and the presence of acentric chromosomes, very long or ring chromosomes which are found in metaphases containing DCC. Algorithms would detect these features at the candidate locations. For example, acentric chromosomes, which lack centromeric constructions, have high cardinality for $W_m(\text{Wid}_{wp} \approx N)$. These features should allow us to reduce the false positives and hence, increase the specificity of detecting cells containing DCC.

We then evaluate performance of feature classification algorithms to detect missing or incorrectly placed centromeres and properly assign their correct positions. This approach works best if the detection process uses multiple cues along with decision making capabilities based on training and past experience. Due to their high morphological variability, the width and intensity profiles of chromosomes are susceptible to noise. This noisy condition can be prominent on Giemsa stained images. Therefore, a decision cannot be made based only on the above two feature profiles. The process considers multiple inputs to make decisions regarding the presence of DCC. We would then implement additional feature detectors based on visual cues used by a geneticist. Detectors include: (a) Relative distance between both centromere locations, (b) Image analysis of the local vicinity of the detected centromere locations, (c) Distance between the centromere locations, (d) Probability of having acentric chromosome fragments (which will be important for ranking and selecting preferred images for analysis that have undergone a single mitotic division), and (e) Presence of ring chromosomes, if any, and determining their frequencies.

This process also attempts to learn from past decisions and incorporate that information into the final decision making stage. The machine learning techniques generally support or reject our hypothesis, which is "that each chromosome is a DCC". The machine learning system would then use above feature detectors and learns to classify DCCs based on manual classification by a geneticist. The first step determines the features that are used for machine learning. Support Vector machines (SVM) and Artificial Neural Networks (ANN) are the primary machine learning algorithms for this purpose. SVM is preferred over ANN, due to SVM being a large-margin classifier and shown to have better performance against back-propagation based ANNs. Although Decision trees lack the granularity of SVMs or ANNs, they are able to work with categorical data (e.g. labels instead of numerical values). The explanation as to why one of these algorithms might give better recall than another is usually determined by the dimensionality of the problem (number of features and their properties) and the spread of the features amongst the image set.

In instances where machine learning techniques do not improve the performance of DCC detection, we would then incorporate fuzzy inference systems that are based on rules dictating the appearance of image features noted by cytogeneticists. The parameter space for classifications may also be constrained with the use of these systems. Expert knowledge is expressed as a set of fuzzy "if-then rules" that apply to DCC based on the appearance of these image features. Partial separation of sister chromatids distal to a centromere and premature centromere separation introduces errors in the chromosome centerline. A rule-based test for concavity of chromosome contours in this region will detect these structures. Erosion of these structures would then eliminate false positive centromere assignments. Another rule indicating cosegregation of dicentric and acentric chromosomes in the same metaphase also increases the accuracy of dicentric detection. Such approaches are known to reject false positives and increase specificity.

Comparing the Performance of Different Chromosome Preparation Procedures for Optimal Automated Dicentric Detection.

Stained cell preparations on microscope slides and suspensions of unstained, fixed cells from blood samples at a series of defined radiation doses are obtained and analyzed. Cell suspensions are spread on microscope slides and stained. Metaphase cells are automatically captured using either a Metasystems or Genetix microscopy systems for each preparation. First division mitotic cells (100-500) are manually selected and scored for the frequency of DCCs. Analysis is done on blinded samples. Imaged cells are analyzed with the centromere detection algorithms of the instant invention and the DCC frequencies compared to the ground truth (scoring by a cytogeneticist).

To prepare a biodosimetry curve, whole blood from 5 healthy donors, with no history of ionizing radiation exposure, and is irradiated for various durations and distances using a Cobalt-60 source. The source has been calibrated with an ion chamber rate (cGy per minute) traceable to the National Research Council of Canada (INMS). The Cobalt Irradiator has a fixed beam orientation pointing up with an exposure build-up tray for cellular exposures. The 1000 Ci source generates a maximum dose rate of ~200 cGy or 2 Gray per minute. Dose rates can be reduced using different distances from the source access port or adding shielding layers of lead.

A dose-response calibration curve in the dose range 0-5.0 Gy is constructed from cultured and harvested irradiated samples using the standard 48 hour culture method with FPG [Fluorescent plus Giemsa] staining (Wilkins R C, et al. Interlaboratory comparison of the DCC assay for radiation biodosimetry in mass casualty events. *Radiation Research* 169: 551-560, 2008). Cell suspensions are spread on microscope slides and stained. Metaphase cells are automatically captured using our Metasystems or Genetix microscopy systems for each preparation. First division mitotic cells (100-500) are manually selected and scored for the frequency of DCCs (Wilkins R C, et al. Interlaboratory comparison of the DCC assay for radiation biodosimetry in mass casualty events. *Radiation Research* 169:551-560, 2008). This FPG method results in uniformly Giemsa stained chromosomes with centromeres detected as constrictions.

Figure 5:
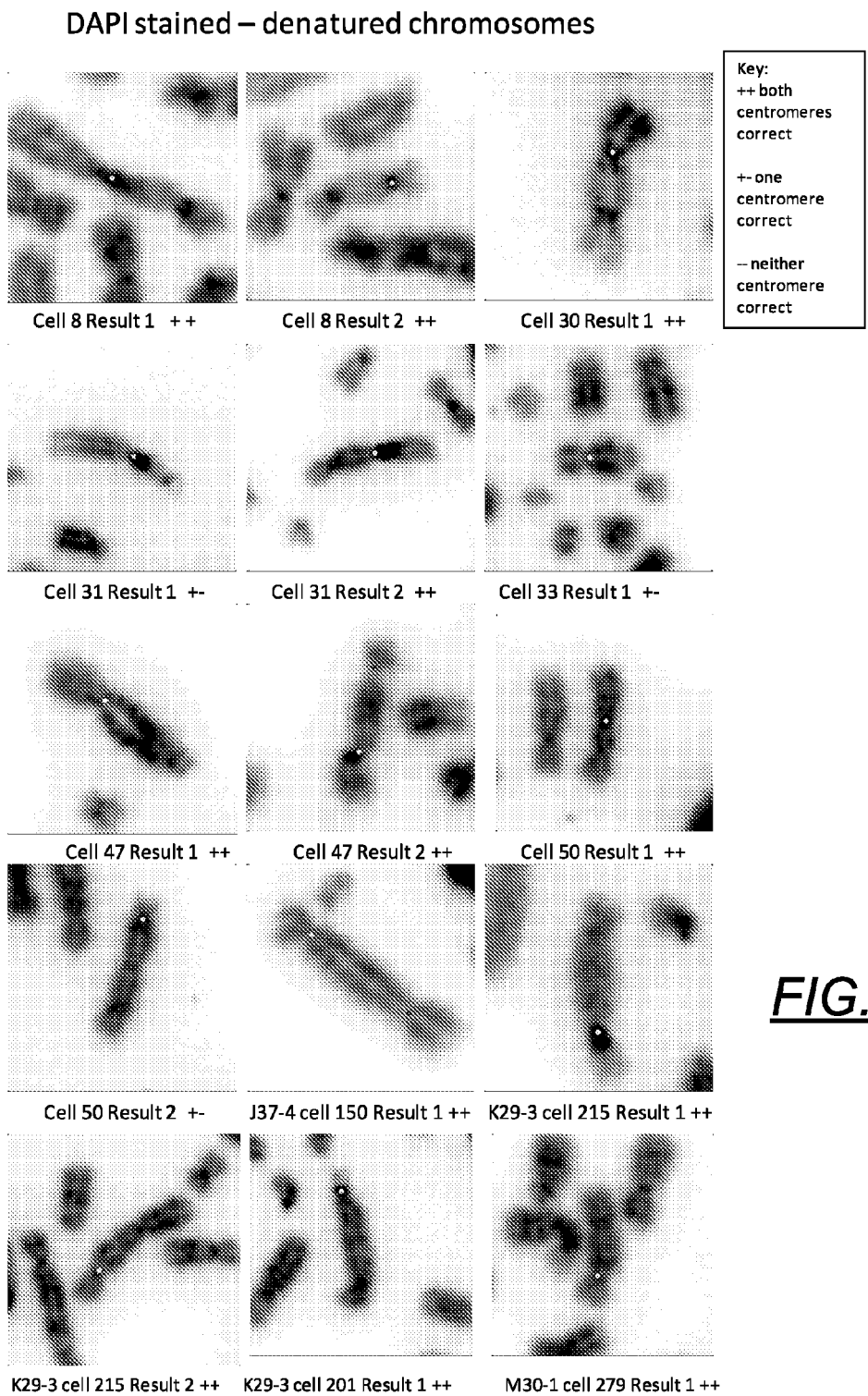
FIG. 5 depicts denatured chromosomes after DAPI staining.
Figure 6:
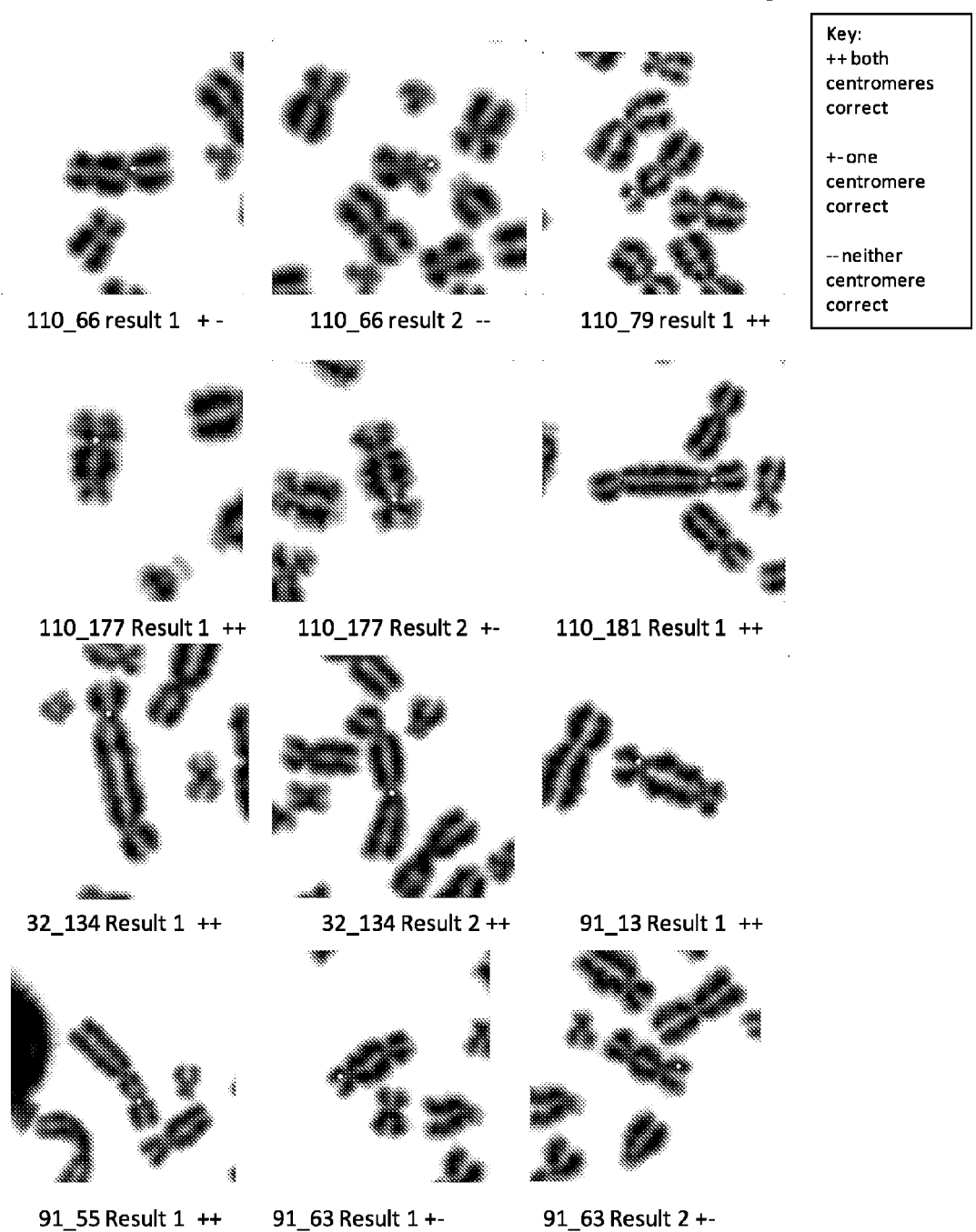
FIG. 6 depicts dicentric scoring of centromeres after Giemsa staining.

To determine the optimal chromosome staining procedure that yields that highest level of DCC detection by image processing algorithms, we will exploit intrinsic features of the centromere that result in staining differences between it and the rest of the chromosome. Our results with DAPI-stained chromosomes suggest that the textural features produced by centromeric DNA sequence and protein composition can improve DCC detection by automated methods. Examples are depicted in FIG. 5. Cells from irradiated samples that have been cultured and fixed using standard biodosimetry methods are subjected to different post-fixation staining methods to accentuate centromeric appearance. By limiting the modifications to cells cultured and fixed in the standard way, it is more likely that they will be adopted for DCC detection by other labs.

(i) C-banding methods (Sumner A T. *Exp Cell Res* 75:304-306, 1972) denature chromatin with barium hydroxide. Heterochromatin, which is primarily located at centromeres, stains dark with Giemsa. The rest of the chromosomes are pale staining. While the method is simple and fast, a non-centromeric portion of the Y chromosome also contains heterochromatin. Rule-based inference is necessary to eliminate this potential source of false positive DCCs in male cells.

(ii) Staining of heat denatured chromosomes with DAPI, a fluorescent dye with increased affinity for A/T-rich sequences, produces characteristic banding along the length of the chromosome with increased fluorescence intensities at centromeres and on the Y chromosome. While also simple and fast, variable centromere staining for the same chromosome can occur in cells at different stages of metaphase portion of the cell cycle.

(iii) Fluorescence in situ hybridization (FISH; J. Knoll and P. Lichter, Unit 4.3, *Current Protocols in Human Genetics*, Wiley NY, 1994, revised 2006) involves hybridizing chromosomes with a pancentromeric, fluorescent DNA probe that is complementary to all centromeres. Centromere hybridizations are readily identifiable, but can vary in size as seen with DAPI alone. FISH is robust, has high sensitivity, and is routinely performed, but does require an additional 4-24 hours for hybridization and detection prior to DCC analysis. (iv) *Immunohistochemistry (IHC) with a fluorescent antibody directed against CENPB*, a centromere-specific protein (Earnshaw W et al. *Chromosoma* 98:1-12, 1989). CENPB is present at all centromeres and is detected by its fluorescence on DAPI-stained chromosomes. This method is sensitive, but also adds several additional hours to the procedure. While centromeres can be discriminated from all other chromosomal structures by FISH and IHC, quantity and cost of DNA probes and CENPB antibodies could limit their application in the event of mass casualty.

These methods can be performed on irradiated cells, and dose-response calibration curves (range 0-5.0 Gy (Wilkins R C, et al. Interlaboratory comparison of the DCC assay for radiation biodosimetry in mass casualty events. *Radiation Research* 169:551-560, 2008)) are constructed by performing linear regression of DCC counts at each dose. By comparing the slopes and residuals for different staining methods, we can determine which methods are equivalent or more sensitive than standard FPG for DCC detection. These methods would then be used to develop the segmentation and training of automated procedures described in Step (2). The observed DCCs from the most sensitive staining protocol(s) are compared to expected ground truth measurements. The number of aberrations observed by the software are compared to the expected number, based on the expected frequencies at a given dose. Aberration data follow a Poisson distribution. Statistical significance (at 95% confidence) between the observed and expected aberrations is assessed by one sample inference for the Poisson distribution, small sample test; critical value method (Rosner B. Hypothesis testing: one sample inference. One sample inference for the Poisson Distribution pp. 237-243. In: *Fundamentals of Biostatistics*, Duxbury Press, Belmont, Calif., 1995). The test can reveal significant differences if the software can produce more false positive DCCs when overlapping chromosomes are not segmented correctly. The software can detect more true positive DCCs, if the automated cell selection criteria aren't as stringent as they are for manual scoring.

Software to Accurately Identify DCC in Optimally Ranked Metaphase Spreads.

A single integrated software program can then be implemented for ranking images, segmenting chromosomes, and detecting dicentric (and acentric) chromosomes, based on the best performing chromosome image analysis and staining methods. This will require integrating individual programs developed in Steps 1 & 2 into a single application (preferably containing vectorized code).

Automated Metaphase Chromosome Centromere Refinement Using Fuzzy Inference Systems Centromere detection processes are in general prone to significant levels of detection error. J. Piper and E. Granum, "On fully automatic feature measurement for banded chromosome classification," Cytometry, vol. 10, pp. 242-255, 1989. X. Wang et al, "A rule-based computer scheme for centromere identification and polarity assignment of metaphase chromosomes," Computer Methods and Programs in Bio Medicine, vol. 89, pp. 33-42, 2008. M. Moradi and S. K. Saterandan, "New features for automatic classification of human chromosomes: A feasibility study," Pattern Recognition Letters, no. 27, pp. 19-28, 2006. P. Mousavi and R. Ward, "Feature analysis and centromere segmentation of human chromosome images using an iterative fuzzy algorithm," IEEE Transactions on Biomedical Engineering, vol. 49, no. 04, April 2002. M. Moradi et al., "Automatic locating the centromere on human chromosome pictures," in 16th IEEE Symposium on Computer-Based Medical Systems, 2003.

Most of these detection errors arise due to noise present in the detected centerline of the chromosome. These noisy data points typically cause the width profile measurements to miss the sharp width change at the constriction. This yields a different position at the centromere. The majority of these deviations are local in nature. i.e.—the detected position and the desired position are close together. Yet, these slight offsets can adversely affect many measurements such as polarity assignment (p and q arm assignment) etc. In detecting dicentric chromosomes, the main importance is in finding the number of centromere locations as opposed to their respective locations. Yet, any false positive centromere location can adversely affect any reasoning process present to detect a dicentric. Therefore, we have proposed a novel 'centromere refinement' process which attempts to correct these small offsets in the detected locations. This in turn will improve the ability to accurately identify dicentric chromosomes. The proposed refining stage utilizes information gathered through previous stages of our algorithm. S. A. Akila et al., "An accurate image processing algorithm for detecting FISH probe locations relative to chromosome landmarks on DAPI stained metaphase chromosome images," Seventh Canadian Conference on Computer and Robot Vision (CRV 2010), May-June 2010.

The proposed refinement process was based on the width profile of the chromosome along the centerline and the intensity or weighted intensity profile along the centerline. This selection increases the adaptability of the proposed refinement process into many existing centromere detection algorithms.

First, the search space for our refinement algorithm was defined. The size of this search space bears a direct relationship with the performance of the algorithm. The following requirements had to be met through setting this value: the region has to be large enough to include the desired centromere location, and the region also must not include the other centromere location (in dicentric chromosomes).

The value was set empirically to 0.20 (of the total length of the chromosome) in order to compromise between the above conditions. Based on the current centromere location, a set of centerline points were selected from the centerline as the search space. Next, a total of 72 line segments covering all 360° were drawn through each of these extracted centerline points. These sets of lines were drawn in order to reasonably cover nearly all possible orientations. The end points of these line segments were detected using the previously extracted binary object contour. This contour was obtained using gradient vector flow (GVF) active contours and local thresholding (S. A. Akila et al., "An accurate image processing algorithm for detecting FISH probe locations relative to chromosome landmarks on dapi stained metaphase chromosome images," Seventh Canadian Conference on Computer and Robot Vision (CRV 2010), May-June 2010.) Then for each line segment, the following three measurements were recorded (refer to FIG. 9). FIG. 9 depicts the setup of line sampling (L1, L2, L3 . . . ) for an interior centerline point P2. Referring to FIG. 9, O-X is the horizontal axis and Q-R is the line perpendicular to P1-P3, through P2. Also the angle measurement for the line segment L1 is depicted. In FIG. 9, P1, P2 and P3 are any 3 consecutive points on a pruned chromosome centerline. L1, L2 and L3 are lines drawn through P2 that are 2.5 degrees apart.

1) ResW—The relative width of the line segment, based on the binary object contour. The ResW value was calculated as a ratio between two measurements as—

$$\left(\frac{\text{width of the line segment}}{\text{average width of the width profile}}\right)$$

Therefore, the 'ResW' values become a relative measure rather than a direct measurement. Thus a particular value of 'ResW' below 1.0 depicts a reasonably suitable candidate for the centromere.

2) ResDA—The angular difference or offset ($\theta_{off}$) between the direction of the line segment and the expected direction given by Q-R (refer FIG. 9). This feature would provide the information regarding the deviation from the original trellis structure (see FIG. 9).

3) ResInt—The average pixel intensity in a 5×5 neighborhood around the candidate centerline pixel. This value was normalized as follows—

$$\left(\frac{\text{average pixel intensity (local neighborhood)}}{\text{maximum average intensity in the search space}}\right)$$

FIG. 9 depicts the setup of line sampling (L1, L2, L3 . . . ) for an interior centerline point P2. Referring to FIG. 9, O-X is the horizontal axis and Q-R is the line perpendicular to P1-P3, through P2. Also the angle measurement for the line segment L1 is depicted.

All data entries were sorted based on the 'ResW' value and the two best (with the lowest ResW) entries were selected along with the ResDA, ResInt values for each selected point. The selection of two best entries was aimed to avoid getting false negatives in the final data set while possibly containing the optimum candidate. Therefore, we end up having (2×n) candidate solutions, where 'n' is the size of the search space.

Next, we need to formulate a method to select the best position for the centromere from the above pool of candidates. The method in question has to be able to embed "expert knowledge" in to the selection process. This will facilitate the centromere detection, which can be a difficult task for even a human eye (untrained). "Fuzzy logic systems" is a well known method formulated to embed a set of "linguistic rules" into the decision making process. Therefore, in this research, we have utilized "zadeh—mamdani type fuzzy logic system" as our decision making framework.

Figure 12:
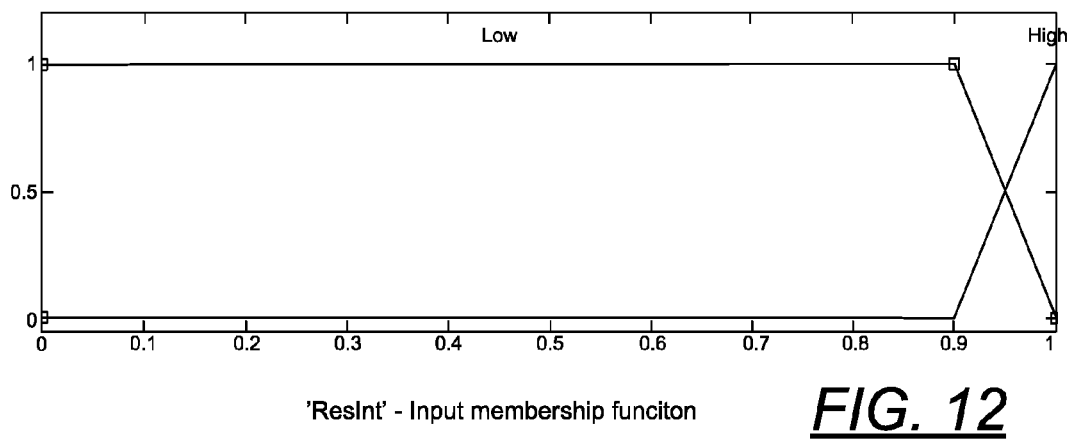
FIG. 12 depicts 'ResInt' input membership function and the shape and parameter information of the output fuzzy membership function.
Figure 13:
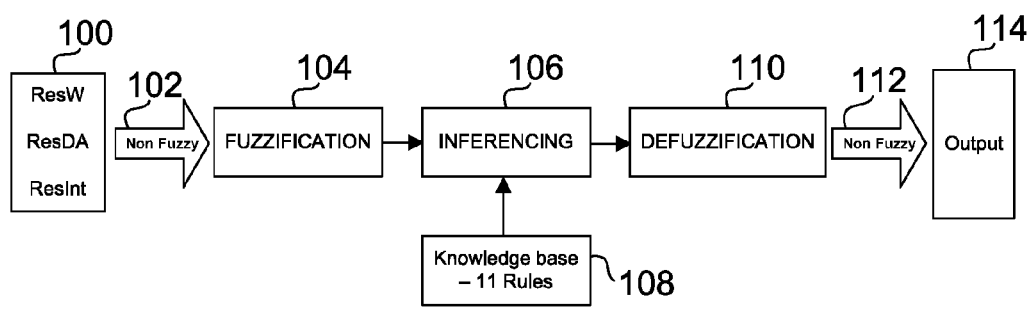
FIG. 13 depicts the basic fuzzy logic setup.

Triangular fuzzy membership functions used were for majority of inputs and the output. The shapes and the parameters of these membership functions are depicted by FIG. 10, FIG. 11 and FIG. 12. A set of fuzzy rules needed to be formulated which accordingly defines the solution space for the system (the output variable). From the features that were used, 'ResDA' and 'ResInt' are mainly for biasing the final result while relying mainly on detecting the constriction from the 'ResW' value. The average intensity feature ('ResInt') in particular was used to bias towards the higher intensity values (in the inverted DAPI image). This formulation makes our proposed algorithm robust in detecting dicentric centromeres, as the sister chromatid separation may cause banding information to become less prominent. These provisions were reflected through the rule set for the fuzzy logic setup. The number of rules and the combinations has to be picked to have an adequate level of generalization while avoiding over fitting. In our method, we derived 11 knowledge based rules to incorporate all these requirements (depicted in table 2). A close observation of table 2 would illustrate the effects of each feature towards the final decision. The final output level (defuzzification) was calculated using the 'centroid' method. The basic fuzzy logic setup is given in FIG. 13. Referring to FIG. 13, The ResW, ResDA, and ResInt (nonfuzzy at this point 102) are fuzzified 104. Eleven knowledge based rules 108 (shown below in Table 2) are applied and inferencing 106 is done, the results of which are defuzzified 110 and converted 112 to the fuzzification output 114.

TABLE 2

If then rules used in the fuzzy logic setup.

| Rule Number | ResW | ResDA | ResInt | Output level |
|---|---|---|---|---|
| 1 | Very Low | Low | — | Ultra High |
| 2 | Very Low | Medium | — | Ultra High |
| 3 | Low | Low | — | Very High |
| 4 | Low | Medium | — | Medium High |
| 5 | Low | High | — | Medium Low |
| 6 | Medium | Low | High | Medium High |
| 7 | Medium | Medium | High | Medium Low |
| 8 | Medium | High | — | Very Low |
| 9 | Medium | Low | Low | Medium Low |
| 10 | Medium | Medium | Low | Very Low |
| 11 | High | — | — | Ultra Low |

The algorithm for determining centromere location based on the fuzzy logic scheme is as follows:

1. From the two sets of fuzzy output results (2 candidate sets per every centerline pixel), the maximum result is selected for each set.

2. Also, the offset (from the current centromere) is also calculated for those 2 best results.

3. We then look at the difference between these two best candidate values (fuzzy output), and check it against a threshold of 0.1

4. If the difference is higher than 0.1, the centerline pixel with the highest result is selected as the new centromere location.

If the difference is lower than 0.1, the centerline pixel with the lowest offset is selected as the new centromere location. The output value is in the range of: 0.0-1.0 (and varies typically for best results between 0.6-0.9). Therefore, a 0.1 improvement between the best two results is a very significant improvement, in which we should neglect the offset.

Figure 14:
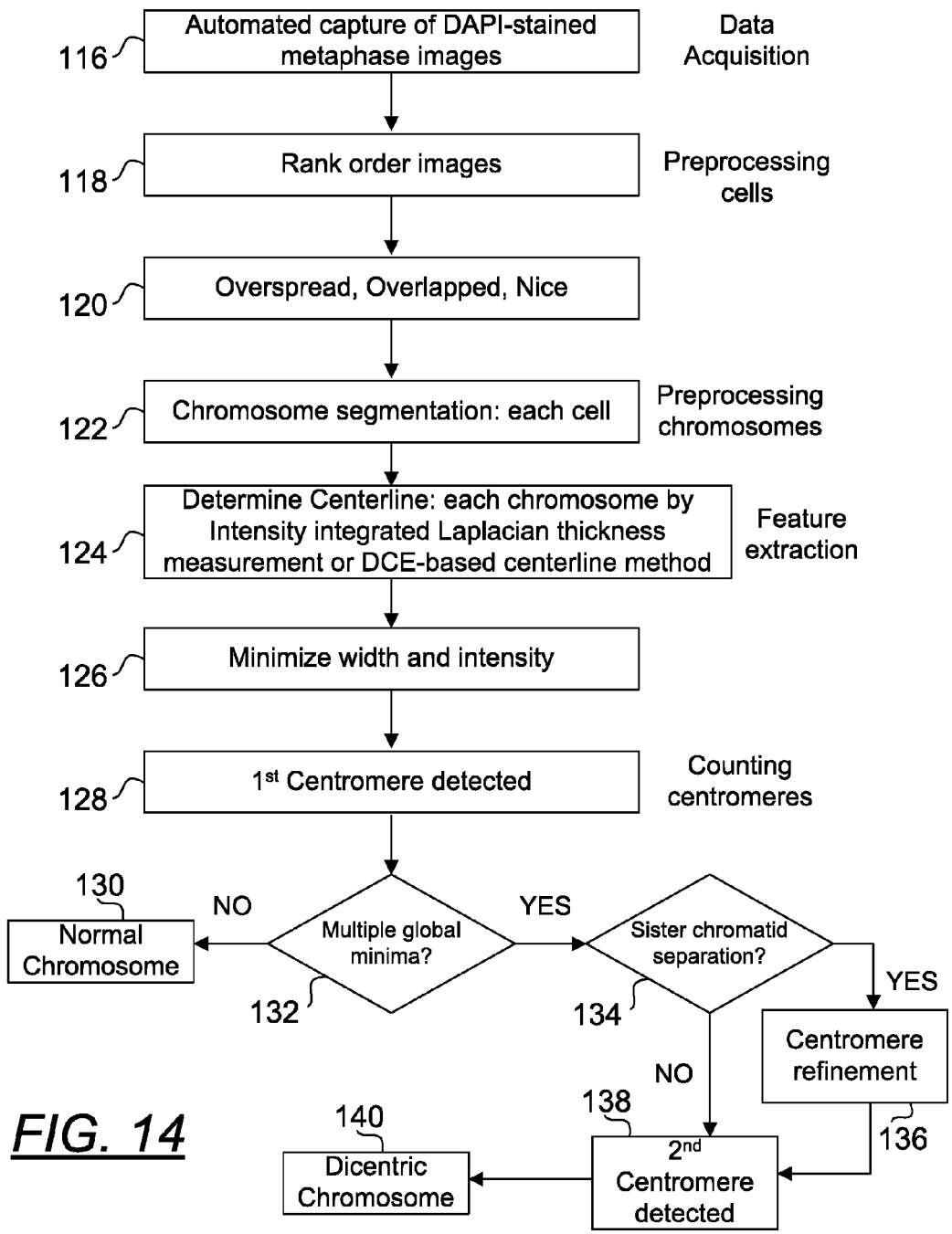
FIG. 14 depicts a novel process according to the present invention.

FIG. 14 depicts a novel process according to the present invention. In step 116, the automated capture of DAPA-stained metaphase images are acquired. The images are ranked ordered 118 in the preprocessing steps, classifying the images as overspread, nice or overlapped 120. The chromosomes are preprocessed 122, segmenting the chromosomes in each cell. The features are extracted 124 and the centerline is determined for each chromosome. The width and intensity are minimized 126. The centromeres are counted 128. If the multiple global 132 is not minimal, then the chromosome is normal 130. If the multiple global 132 is minimal, then we look for sister chromatid separation 134. If we find it, we refine the centromere 136. If we do not find it, then the second centromere is detected 138 and we have a dicentric chromosome 140.

Thus, there is also disclosed a computer program product stored in a computer storage means, said computer program product operable for deriving parameters for a fuzzy logic system, wherein said fuzzy logic system is adapted for determining a location of at least one centromere of each chromosome in a cell in at least one image of a metaphase nuclei, said computer program product comprising: means for accessing an algorithm to produce a plurality of candidate chromosome centerlines representing said parameters for said fuzzy logic system, said parameters including input membership functions and rules for said fuzzy logic system; means for transforming each of said plurality of candidate chromosome centerline into said parameters for said fuzzy logic system; means for importing said parameters into said fuzzy logic system for said each of said plurality of candidate chromosome centerline; means for simulating said fuzzy logic system with respect to said each of said plurality of candidate chromosome centerline, wherein said simulating means further comprises: means for producing image data of said metaphase nuclei cell to be recognized by said fuzzy logic system, means for inputting said image data into a learning vector quantization network to produce optimized moment invariant vectors associated with each of said fuzzy logic system, and means for inputting said optimized moment invariant vectors into said fuzzy logic system; means for evaluating said simulations with respect to a threshold parameter; and means for selecting one of said plurality of candidate chromosome centerline resulting from said evaluating means if said one of said plurality of candidate chromosome centerline satisfies said threshold parameter.

There is also disclosed a method for deriving parameters for a fuzzy logic system adapted for determining a location of at least one centromere of each chromosome in a cell in at least one image of a metaphase nucleus, said method comprising the steps of:

producing image data of centromeres to be recognized by fuzzy logic system application; inputting said image data into a learning vector quantization network to produce optimized moment invariant vectors associated with each of said fuzzy logic system; accessing an algorithm to produce a plurality of candidate chromosome centerline representing said parameters for said fuzzy logic system; transforming each of said plurality of candidate chromosome centerline into said parameters for said fuzzy logic system; importing said parameters into said fuzzy logic system for said each of said plurality of candidate chromosome centerline; simulating said fuzzy logic system with respect to said each of said plurality of candidate chromosome centerline; inputting said optimized moment invariant vectors into said fuzzy logic system; with respect to said each of said plurality of candidate chromosome centerline, determining how many of said centromeres are correctly recognized by said fuzzy logic system; selecting one of said plurality of candidate chromosome centerline if said one of said plurality of candidate chromosome centerline correctly recognizes all of said centromeres; associating a score with said each of said plurality of candidate chromosome centerline, said score indicating how many of said centromeres were recognized by said each of said plurality of candidate chromosome centerline; selecting a percentage of said plurality of candidate chromosome centerline having better scores; applying a crossover process between said selected percentage of said plurality of candidate chromosome centerline to produce one or more children; replacing one or more of said plurality of said candidate chromosome centerline having worst scores with said one or more children, resulting in a new population of candidate chromosome centerline; transforming said new population into fuzzy logic parameters; importing said fuzzy logic parameters of said new population into said fuzzy logic system; simulating said fuzzy logic system with respect to said new population; inputting said optimized moment invariant vectors into said fuzzy logic system; with respect to each of said plurality of candidate chromosome centerline in said new population, determining how many of said centromeres are correctly recognized by said fuzzy logic system; and selecting one of said plurality of candidate chromosome centerline in said new population if said one of said plurality of candidate chromosome centerline in said new population correctly recognizes all of said centromeres.

There is also disclosed a set of instructions stored on at least one non-transitory computer readable medium for running on a computer system, comprising: instructions for receiving one or more electronic files of images into one or more memory; instructions for identifying image content resembling a metaphase nucleus containing discrete, adjacent chromosomes; instructions for identifying metaphase chromosomes and portions thereof in the image content; instructions for determining local classification parameters of metaphase chromosomes and chromosomes connected to neighboring chromosomes; instructions for extracting chromosome features from the image content; instructions for applying a classification system based on extracted chromosome features to the image content to separate a plurality of different categories of images, the categories consisting of a nice classification, an overlapped classification, and an overspread classification, wherein a nice classification is an image having at least one chromosome that is fully contained in the image and having substantially no overlap with another chromosome, an overlapped classification is an image having at least two chromosomes that are superimposed on one another, and an overspread classification is an image having at least one chromosome that is only partially contained in the image sector; instructions for applying a ranking system to the images based upon a plurality of global parameters; instructions for selecting a subset of images based upon rank; instructions for determining contours of the chromosome; instructions for determining the location of the centerline of the chromosome; instructions for locating the most likely position of at least one centromere in the chromosome, whereby a plurality of chromosomes in the same cell are classified based on position; instructions for measuring a centromere confidence value to measure the probable location of the automated centromere detection process; instructions for masking the most likely location for the first centromere and recomputing the centromere confidence value to determine if subsequent centromeres are present on the same chromosome; instructions for counting the number of centromeres in the chromosome; instructions for computing a frequency of dicentric chromosomes in at least one cell; and instructions for determining a radiation dose by comparing the computed frequency of each dicentric chromosome with a previously determined dose-response curve from a calibrated source.

In one aspect, there is the instructions a.-p. are adapted to be executed without manual intervention. There is generally at least one instruction for storing information indicative of the content resembling a metaphase chromosome. In one aspect, there is at least one instruction for storing information for determining local classification parameters of metaphase chromosomes and chromosomes connected to neighboring chromosomes. In one aspect, there is at least one instruction for storing global ranking parameters of metaphase chromosomes and chromosomes connected to neighboring chromosomes. In one aspect, there is at least one instruction for storing the ranked images. In one aspect, there is at least one instruction for storing contours of chromosomes. In one aspect, there is at least one instruction for storing the location of the centerline of metaphase chromosomes. In one aspect, there is at least one instruction for storing the number of centromeres in a metaphase chromosome. In one aspect, there is at least one instruction for storing the location of centromeres in a metaphase chromosome. In one aspect, there is at least one instruction for storing a determination of an abnormal chromosome. The instructions are adapted to determining the frequency of dicentric chromosomes in a set of images of metaphase nuclei. The instructions are adapted to determining the centromere confidence value to determine the most probable locations of one or more centromeres in a chromosome. The instructions are adapted to determining a radiation dose by comparing the computed frequency of each dicentric chromosome with a previously determined dose-response curve from a calibrated source.

Example 1

Automatic Detection of Individual Centromeres in Normal Chromosomes

Cells from three different normal individuals were imaged by fluorescent microscopy after heat denaturing fixed metaphase chromosomes in 2×SSC, 50% formamide, 10% dextran sulfate solution and staining with DAPI (as described in J. Knoll and P. Lichter, Unit 4.3, *Current Protocols in Human Genetics*, Wiley NY, 1994, revised 2006). Grayscale images were obtained with a DAPI filter set using an Olympus BX61 microscope and Cytovision Software (Genetix Inc, San Joe, Calif.) and inverted. Denaturation enhances staining of centromeric and heterochromatic sequences (in contrast with single copy euchromatic domains) because of the preference of this dye for binding to double stranded A/T rich DNA which reforms due to self-renaturation of tandem alphoid monomers in these regions. Digitally captured images were then inverted, and partial metaphase regions containing well separated chromosomes were segmented to obtain their cardinal features required for centromere localization. The coordinates of the centromeres determined from the segmented chromosome features are given in the following table. These inferred locations of the centromeres were assessed by two cytogeneticists to determine the accuracy of the instant method:

| Microscope Slide No. | Cell No. | Centromere coordinates (pixels) X | Y | Partial metaphase coordinates X | Y | Correct Location? |
| --- | --- | --- | --- | --- | --- | --- |
| 1974 | 1 | 112 | 91 | 374.45 | 306.52 | Yes |
| 1974 | 2 | 101 | 99 | 348.00 | 364.72 | Yes |
| 1974 | 3 | 99 | 97 | 400.91 | 479.37 | Yes |
| 1974 | 4 | 94 | 99 | 377.98 | 551.68 | Yes |
| 1974 | 5 | 100 | 99 | 429.13 | 631.05 | Yes |
| 1974 | 6 | 108 | 97 | 547.30 | 599.30 | Yes |
| 1974 | 7 | 100 | 98 | 609.04 | 572.85 | Yes |
| 1974 | 8 | 100 | 101 | 496.15 | 595.78 | Yes |
| 1974 | 9 | 110 | 110 | 669.00 | 477.60 | Yes |
| 1974 | 10 | 99 | 98 | 580.81 | 392.94 | No |
| 1974 | 11 | 102 | 106 | 536.72 | 366.48 | Yes |
| 1974 | 12 | 94 | 96 | 577.29 | 350.61 | Yes |
| 1974 | 13 | 99 | 100 | 531.43 | 322.39 | Yes |
| 1974 | 14 | 109 | 91 | 402.67 | 362.96 | Yes |
| 1974 | 15 | 107 | 98 | 388.56 | 433.51 | Yes |
| 1974 | 16 | 93 | 106 | 515.56 | 463.49 | Yes |
| 1974 | 17 | 110 | 97 | 485.57 | 502.30 | Yes |
| 1974 | 18 | 86 | 102 | 566.70 | 551.68 | Yes |
| 1974 | 19 | 101 | 91 | 630.20 | 479.37 | Yes |
| 1974 | 20 | 103 | 100 | 446.77 | 461.73 | Yes |
| 1974 | 21 | 93 | 104 | 480.28 | 467.02 | Yes |
| 1974 | 22 | 98 | 89 | 582.58 | 294.17 | Yes |
| 1974 | 23 | 97 | 93 | 499.68 | 535.81 | Yes |
| 1973 | 1 | 108 | 91 | 436.19 | 308.28 | Yes |
| 1973 | 2 | 88 | 105 | 506.74 | 306.52 | Yes |
| 1973 | 3 | 115 | 99 | 434.42 | 345.32 | Yes |
| 1973 | 4 | 113 | 89 | 339.18 | 472.31 | Yes |
| 1973 | 5 | 95 | 105 | 386.80 | 549.92 | Yes |
| 1973 | 6 | 104 | 104 | 381.51 | 608.12 | Yes |
| 1973 | 7 | 107 | 102 | 473.22 | 548.15 | Yes |
| 1973 | 8 | 95 | 104 | 598.45 | 611.65 | Yes |
| 1973 | 9 | 86 | 93 | 639.02 | 620.47 | Yes |
| 1973 | 10 | 112 | 87 | 658.42 | 534.04 | Yes |
| 1973 | 11 | 99 | 105 | 557.89 | 519.93 | Yes |
| 1973 | 12 | 96 | 94 | 593.16 | 366.48 | Yes |
| 1973 | 13 | 94 | 100 | 494.39 | 361.19 | Yes |
| 1973 | 14 | 101 | 106 | 459.11 | 407.05 | Yes |
| 1973 | 15 | 102 | 102 | 561.41 | 396.47 | Yes |
| 1973 | 16 | 102 | 99 | 407.96 | 451.15 | Yes |
| 1973 | 17 | 99 | 104 | 674.30 | 602.83 | Yes |
| 1973 | 18 | 109 | 101 | 531.43 | 572.85 | Yes |
| 1973 | 19 | 103 | 105 | 594.93 | 528.75 | Yes |
| 1972 | 1 | 95 | 102 | 485.57 | 299.46 | Yes |
| 1972 | 2 | 92 | 103 | 356.81 | 362.96 | Yes |
| 1972 | 3 | 101 | 107 | 360.34 | 384.12 | Yes |
| 1972 | 4 | 110 | 94 | 409.73 | 359.43 | Yes |
| 1972 | 5 | 103 | 95 | 441.48 | 355.90 | Yes |
| 1972 | 6 | 103 | 105 | 418.55 | 431.74 | Yes |
| 1972 | 7 | 99 | 94 | 383.27 | 461.73 | Yes |

-continued

| Microscope Slide No. | Cell No. | Centromere X | coordinates (pixels) Y | Partial metaphase X | coordinates Y | Correct Location? |
|---|---|---|---|---|---|---|
| 1972 | 8 | 109 | 91 | 340.94 | 484.66 | Yes |
| 1972 | 9 | 97 | 103 | 353.29 | 447.62 | Yes |
| 1972 | 10 | 105 | 98 | 363.87 | 539.33 | Yes |
| 1972 | 11 | 125 | 103 | 473.22 | 442.33 | No |
| 1972 | 12 | 99 | 103 | 450.30 | 498.77 | Yes |
| 1972 | 13 | 93 | 100 | 474.99 | 606.36 | Yes |
| 1972 | 14 | 107 | 93 | 568.47 | 602.83 | Yes |
| 1972 | 15 | 100 | 100 | 573.76 | 514.64 | Yes |
| 1972 | 16 | 108 | 94 | 630.20 | 518.17 | Yes |
| 1972 | 17 | 106 | 102 | 480.28 | 401.76 | Yes |
| 1972 | 18 | 91 | 110 | 531.43 | 382.36 | Yes |
| 1972 | 19 | 119 | 107 | 630.20 | 359.43 | Yes |
| 1972 | 20 | 95 | 102 | 582.58 | 315.33 | Yes |
| 1972 | 21 | 100 | 103 | 575.52 | 340.03 | Yes |
| 1972 | 22 | 102 | 97 | 647.84 | 544.63 | Yes |
| 1972 | 23 | 108 | 110 | 494.39 | 362.96 | Yes |
| 1972 | 24 | 99 | 108 | 575.52 | 405.29 | Yes |
| 1972 | 25 | 98 | 116 | 651.37 | 412.34 | Yes |
| 1970 | 1 | 88 | 103 | 446.77 | 311.81 | Yes |
| 1970 | 2 | 88 | 102 | 392.09 | 341.79 | No |
| 1970 | 3 | 94 | 110 | 392.09 | 370.01 | Yes |
| 1970 | 4 | 92 | 96 | 415.02 | 408.81 | Yes |
| 1970 | 5 | 100 | 99 | 437.95 | 398.23 | Yes |
| 1970 | 6 | 91 | 110 | 355.05 | 458.20 | Yes |
| 1970 | 7 | 90 | 92 | 415.02 | 507.59 | Yes |
| 1970 | 8 | 98 | 107 | 407.96 | 548.15 | Yes |
| 1970 | 9 | 97 | 108 | 430.89 | 576.37 | Yes |
| 1970 | 10 | 89 | 100 | 473.22 | 528.75 | Yes |
| 1970 | 11 | 99 | 91 | 460.88 | 461.73 | Yes |
| 1970 | 12 | 103 | 109 | 499.68 | 398.23 | Yes |
| 1970 | 13 | 97 | 102 | 631.96 | 375.30 | Yes |
| 1970 | 14 | 94 | 93 | 513.79 | 486.42 | Yes |
| 1970 | 15 | 97 | 98 | 557.89 | 500.53 | Yes |
| 1970 | 16 | 92 | 97 | 605.51 | 475.84 | Yes |
| 1970 | 17 | 100 | 104 | 534.96 | 315.33 | Yes |

Example 2

Results of Centromere Detection Algorithm for Dicentric Detection

Figure 4:
FIG. 4 depicts centromere detection (dots and arrows) by algorithm with Giemsa stain.

The algorithm was developed and tested on DAPI-stained irradiated metaphase chromosome images, and then adapted for FPG stained images. Metaphase spreads from cells were irradiated with 5 Gy of ionizing radiation by Dr. Ruth Wilkins (Health Canada; HC), then heat denatured, and stained with DAPI at Univ. Western Ontario (UWO). We then identified DCC manually and applied a modification of our published algorithm to detect centromeres (Subasinghe A et al. *Canadian Conf. on Computer & Robot Vision*, pp 223-230, DOI: 10.1109/CRV.2010.36, 2010). After segmenting the chromosome and computing the centerline according to the method described infra, the software determines the centromere and the associated CCF values. The first centromere is then masked, and the process is repeated to find the second one. Typical examples of the two centromeres found by the algorithm are marked in FIGS. 3 and 4. Of 20 DCC, 17 (85%) have both centromeres correctly placed. Masking involves removing the width profile entries of the object being masked (in this case the first centromere) from the subsequent calculations to find the next best location for a centromere.

The algorithm was then modified to detect Giemsa or FPG-stained chromosomes that are produced with standardized biodosimetry protocols. These procedures result in nearly uniform staining along the chromosome length, so that pixel intensity is no longer a reliable feature. Images of metaphase cells were processed from blood leukocytes exposed to 5 Gy gamma irradiation at the Chalk River Laboratory (AECL). The AECL protocol results in significant sister chromatid separation, except at centromeric regions. Centromere separation and association between short arms of acrocentric chromosomes can occur, which can confound the automated image analysis. The image processing algorithm was modified to disregard pixel intensities. The second centromere was detected by masking the width profile region containing the first, and the minimum, $W_m$, was redetermined in Wp(i). Of 21 DCC identified by a cytogeneticist, both centromeres were assigned accurately in 15 cells (71%), one centromere accurately in 4, and neither centromere was correctly localized in 2 cases. A second independently collected set of 12 Giemsa-stained dicentric chromosomes was then analyzed and the results were comparable to the first set (7 in which both centromeres were correctly assigned, 4 in which one was correctly assigned, and 1 with neither centromere being correct).

Whereas separation of the sister chromatids doesn't significantly affect the width profile in DAPI-stained chromosomes, separation is a significant source of error in Giemsa stained chromosomes obtained with extended colcemid treatment. Short, highly condensed chromosomes that exhibit splaying of the sister chromatids at their ends are prone to error because discrete curve evolution ("DCE") misinterprets the single chromatid in this region as the entire chromosome in skeletonizing the centerline. This type of chromosome structure can be distinguished through the unique concave pattern formed by this structure. When concavity is detected, the chromosome contour can be eroded to the point at which this concavity is eliminated (the chromatids fuse). This is the location of a centromere.

Heat denaturation of chromosomal DNA followed by DAPI staining gives better accuracy using the algorithm. Results were obtained that directly compare the algorithm's accuracy for chromosomes that have been heat denatured and stained with DAPI vs. normal chromosomes that were not heat denatured. The results are summarized in the following table:

| Date | Folder | Cell ID | 0/2 correct | 1/2 correct | 2/2 correct | Notes |
|---|---|---|---|---|---|---|
| | | Dicentric Analysis Results - Scoring Oct. 26th, 2010 | | | | |
| N/A | HTAECL DICENTRIC RESULT IMAGES | 21__284__possibleTIClabelled.TIF__result__1 | x | | | Giemsa stained, 5 gy exposure |
| | | 21__284__possibleTIClabelled.TIF__result__2 | | | x | |
| | | 21__342 labelled.TIF__result__1 | | | x | |
| | | 21__342 labelled.TIF__result__2 | | | x | |
| | | 21__342 labelled.TIF__result__3 | | | x | |
| | | 21__352 labelled.TIF__result__1 | | | x | |
| | | 21__352 labelled.TIF__result__2 | | x | | |
| | | 21__352 labelled.TIF__result__3 | | x | | |
| | | 21__358 labelled.TIF__result__1 | | | x | |
| | | 21__428 labelled.TIF__result__1 | | | x | |
| | | 21__428 labelled.TIF__result__2 | | | x | |
| | | 21__428 labelled.TIF__result__3 | | | x | |
| | | 21__441 labelled.TIF__result__1 | | x | | |
| | | 21__441 labelled.TIF__result__2 | | x | | |
| | | 34__297 labelled.TIF__result__1 | | | x | |
| | | 34__297 labelled.TIF__result__2 | | x | | |
| | | 34__297 labelled.TIF__result__3 | | | x | |
| | | 34__589 labelled.TIF__result__1 | | | x | |
| | | 34__664 labelled.TIF__result__1 | | | x | |
| | | 34__664 labelled.TIF__result__2 | | | x | |
| | | 34__902 labelled.TIF__result__1 | | | x | |
| | | TOTALS | 1 | 5 | 15 | |
| Oct. 13, 2010 | RESULTS - Spreads Labeled - Oct. 13, 2010 | 110__66.TIF__result__1 | | x | | Giemsa stained, 5 Gy exposure |
| | | 110__66.TIF__result__2 | x | | | |
| | | 110__79.TIF__result__1 | | | x | |
| | | 110__177.TIF__result__1 | | | x | |
| | | 110__177.TIF__result__2 | | x | | |
| | | 110__181.TIF__result__1 | | | x | |
| | | slide32__134.TIF__result__1 | | | x | |
| | | slide32__134.TIF__result__2 | | | x | |
| | | slide91__13.TIF__result__1 | | | x | |
| | | slide91__55.TIF__result__1 | | | x | |
| | | slide91__63.TIF__result__1 | | x | | |
| | | slide91__63.TIF__result__2 | | x | | |
| | | TOTALS | 1 | 4 | 7 | |
| Oct. 15, 2010 | RESULTS - Spreads Labeled - Oct. 15, 2010/ Denatured Results | Cell 16 Raw.TIF | | | x | DAPI stained, denatured chromosomes (2 minutes at 70° C. in 70% formamide/ 2x SSC) |
| | | Cell 17 Raw.TIF | | | x | |
| | | G37 0__cell 70 Raw.TIF__result__1 | | | x | |
| | | G37 0__cell 70 Raw.TIF__result__2 | | | x | |
| | | H30 3__cell 108 Raw. TIF__result__1 | | | x | |
| | | J28 4__cell 211 Raw.TIF__result__1 | | | x | |
| | | J38 4__cell 169 Raw.TIF__result__1 | | | x | |
| | | J38 4__cell 169 Raw.TIF__result__2 | | | x | |
| | | K33 3__cell222 Raw.TIF__result__1 | | | x | |
| | | K33 3__cell222 Raw.TIF__result__2 | | x | | |
| | | K34 3 cell 226 Raw.TIF__result__1 | | | x | |
| | | K34 3 cell 226 Raw.TIF__result__2 | | | x | |
| | | K34 3 cell 226 Raw.TIF__result__3 | | | x | |

-continued

Dicentric Analysis Results - Scoring
Oct. 26th, 2010

| Date | Folder | Cell ID | 0/2 correct | 1/2 correct | 2/2 correct | Notes |
|---|---|---|---|---|---|---|
| | | M34 1_cell 262 Raw.TIF_result_1 | | x | | |
| | | M34 1_cell 262 Raw.TIF_result_2 | | | x | |
| | | TOTALS | 0 | 4 | 11 | |
| Oct. 15, 2010 | RESULTS - Spreads Labeled - Oct. 15, 2010/ Non-Denatured Results | E24 0_cell 11 Raw. TIF_result_1 | | x | | DAPI stained, no denaturation of chromosomes |
| | | E24 0_cell 11 Raw. TIF_result_2 | | x | | |
| | | E24 0_cell 11 Raw. TIF_result_3 | | x | | |
| | | F24 3_cell 72 Raw.TIF_result_1 | N/A | | | *May be two chromosomes close together as opposed to a dicentric |
| | | F24 3_cell 72 Raw.TIF_result_2 | | | x | |
| | | F27 2_cell 31 Raw.TIF_result_1 | | | x | |
| | | F27 2_cell 31 Raw.TIF_result_2 | | x | | |
| | | F27 2_cell 31 Raw.TIF_result_3 | | | x | |
| | | J39 4_cell 100 Raw.TIF_result_1 | | | x | |
| | | J42 0_cell 50 Raw.TIF_result_1 | | x | | |
| | | J42 0_cell 50 Raw.TIF_result_2 | | x | | |
| | | J42 0_cell 50 Raw.TIF_result_2 | | x | | |
| | | J45 0_cell 33 Raw.TIF_result_1 | | | x | |
| | | J45 0_cell 33 Raw.TIF_result_2 | x | | | |
| | | M40 4_cell 346 Raw.TIF_result_1 | | | x | |
| | | TOTALS | 1 | 7 | 6 | |

We claim:

1. A method for determining radiation exposure from chromosome abnormalities present in a specimen comprising the steps of:
    (a) determining a location of at least one centromere of each chromosome in a cell in an image of a metaphase nucleus by:
        (i) segmenting an accurately drawn chromosome centerline of each of the chromosomes in the cell,
        (ii) selecting a longitudinal cross-section of a chromosome image with a minimum width, intensity or a combination of features derived from width and intensity, wherein in a dicentric chromosome, a location of a first centromere is masked to identify a subsequent longitudinal cross-section with a second lowest minimum of combined width;
    (b) counting the number of centromeres in each chromosome in said cell;
    (c) computing a computed frequency of dicentric chromosomes in a plurality of said cells; and
    (d) determining a radiation dose by comparing the computed frequency of dicentric chromosomes with a previously determined dose-response curve from a calibrated source of ionizing radiation.

2. The method of claim 1, where the location of a first centromere is masked to identify a subsequent longitudinal cross-section of a second centromere with a second lowest minimum of combined width and intensity.

3. The method of claim 1 or 2, where the image of the metaphase nucleus is selected which has at least one of the following properties:
    (i) complete chromosome number,
    (ii) minimize a degree of overlap and intersection of chromosomes, and
    (iii) the chromosomes exhibit defined boundaries.

4. The method of claim 1 or 2, where the centromere location is determined from the cross-sectional intensity and/or width profiles of the chromosome perpendicular to the chromosome centerline.

5. The method of claim 1 or 2, where the chromosome centerline is derived by discrete curve evolution based skeleton pruning.

6. A method of determining a radiation dose comprising the steps of:
    scanning a plurality of sectors in a predetermined area of a microscope slide for at least one sector containing image content similar in morphology to a metaphase cell nucleus containing discrete, adjacent chromosomes thereby creating an image sector;
    identifying metaphase chromosomes and portions thereof in the image content of the image sector;
    determining local classification parameters of metaphase chromosomes and chromosomes connected to neighboring chromosomes;
    extracting features from the image sector of metaphase chromosomes and chromosomes connected to neighboring chromosomes;

applying a classification system based on the extracted chromosome features to separate a plurality of different categories of image sectors, the categories consisting of a nice classification, an overlapped classification, and an overspread classification, wherein
    a nice classification is an image sector having at least one chromosome that is fully contained in the image sector and having substantially no overlap with another chromosome,
    an overlapped classification is an image sector having at least two chromosomes that are superimposed on one another, and
    an overspread classification is an image sector having at least one chromosome that is only partially contained in the image sector;
determining at least once local parameter for each image sector;
applying a ranking system based on a plurality of global parameters;
selecting the image sector having at least one chromosome based on the ranking system wherein the selected image sector has a high rank;
determining at least one contour of the at least one chromosome;
determining a centerline of the at least one chromosome;
locating a most likely position of at least one centromere in the at least one chromosome, whereby a plurality of chromosomes in a cell are classified based on position;
measuring a centromere confidence value to measure a probable location of the at least one centromere;
masking the most likely location for a first centromere and recomputing a centromere confidence value to determine if subsequent centromeres are present on the chromosome;
counting the number of centromeres in the chromosome;
computing a computed frequency of dicentric chromosomes in at least one cell; and
determining a radiation dose by comparing the computed frequency of each dicentric chromosome with a previously determined dose-response curve from a calibrated source.

7. The method of claim 6, wherein the global classification parameters comprise at least one parameter selected from a group consisting of an average area, a standard deviation of the area, length, perimeter, aspect ratio, pairwise distance between each chromosome, and combinations thereof.

8. The method of claim 6, wherein the local ranking parameters comprise at least one parameter selected from a group consisting of total area, ratio of severe overlaps, mean pairwise distance, brightness, contrast, and combinations thereof.

9. The method of claim 6, wherein the step of selecting an image sector comprises providing an algorithm using a fuzzy logic system to detect an abnormal dicentric chromosome.

10. The method of claim 6, wherein determining the contour comprises the steps of:
    a) pre-processing a fluorescent metaphase image of a 4',6-diamidino-2-phenylindole (DAPI)-stained chromosome for chromosome segmentation;
    b) observing an intensity variation of the chromosome;
    c) performing gray scale conversion;
    d) extracting a rectangular shaped window that includes the chromosome and an adjacent background, whereby variations in lighting across the image were alleviated;
    e) normalizing intensities by window center adjustment and mapping across a complete spectrum of possible pixel values;
    f) applying a threshold based on Otsu's method, whereby a binary image is generated;
    g) subjecting the binary image to the content and classification-based ranking algorithm;
    h) applying a scaling factor to the binary image;
    i) extracting the chromosome from the image by connected component labeling of a 4-connected graph, whereby discontinuities were removed within and at the boundary of the chromosome;
    j) tracing the initial chromosome contour using a 3×3 neighborhood; and
    k) applying an active contour to determine the chromosome outline, whereby the active contour iteratively converges towards a closest local minima of image gradients from an initial set of control points.

11. The method of claim 10, further including an iterated Gradient Vector Flow (GVF) active contour to smooth a boundary map of the binary image.

12. The method of claim 6, wherein defining the contour comprises obtaining a thickness profile and a width profile of the chromosome using an intensity integrated Laplacian thickness measurement, whereby a Laplacian operator ($\Delta$) yields the second order derivative of the image thereby emphasizing the chromosome contour information.

13. The method of claim 6, wherein defining the contour comprises using a method of image intensity integration, whereby the image is segmented into a plurality of regions or at least one edge fragment is detected by using a concept of light flux per unit area.

14. The method of claim 6, wherein determining the centerline of the chromosome comprises a skeleton pruning method based on a discrete curve evolution calculation to produce a pruned skeleton, comprising the steps of:
    a) modeling the skeleton as a polygon with a predetermined number of vertices,
    b) partitioning at least one discrete curve evolution contour into polygonal sections,
    c) removing a plurality of skeletal points that generate at least one point on the polygonal section, whereby the resulting skeleton will have a single spurious branch,
    d) providing a curve fitting method, and
    e) sampling control points from the pruned skeleton.

15. The method of claim 6, wherein the step of locating a most likely position of each centromere comprises the steps of:
    a) using an end pruned centerline as a reference, whereby the end pruned centerline excludes at least one maximum end of the chromosome,
    b) drawing at least one trellis line segment perpendicular to the pruned centerline segment at unit length intervals, whereby a predetermined cross sectional is a length of the trellis line segment,
    c) weighting at least one sample intensity of the trellis line segment with a Gaussian function, whereby cancelling a plurality of image noise and a plurality of undesirable effects introduced by chromosome bending,
    d) determining the lengths of the trellis line segments from at least one binary result obtained through a Gradient Vector Flow (GVF) binary image, wherein the GVF binary image is a Gaussian kernel active contour, whereby use of the GVF binary image provides enhanced edge characteristics of the centromere, and
    e) locating the centromere by using Wp, wherein Wp is a width profile of the chromosome, along the trellis line segment on a medial axis of the GVF binary image and Ip, wherein Ip is an intensity profile obtained by getting the weighted average of intensity values of a 4',6-diamidino-2-phenylindole (DAPI)-stained chromosome image based on a Gaussian function along the GVF binary image limited trellis line segment.

16. The method of claim 6, wherein the step of locating a most likely position of each centromere comprises the steps of:
  a) combining a chromosome width with a centerline pixel intensity, and
  b) using a thickness-based measurement alone, whereby a centromere is accurately detected.

17. The method of claim 6, wherein an algorithm using a fuzzy logic system calculates an optimal position for each centromere, the algorithm comprising the steps of:
  a) obtaining a set of line segments covering multiple angles with an angle offset of 2.5° for each centerline pixel in the vicinity of the detected centromere location;
  b) selecting the two shortest line segments from the set of line segments, thereby creating two candidate sets, wherein a first candidate set of the two candidate sets comprises line segments with the shortest value and a second candidate set of the two candidate sets comprises the second shortest line segments;
  c) determining ResDA wherein ResDA is an angular difference between a direction of a line segment and an expected direction from the centromere for the two candidate sets;
  d) calculating an offset value for a plurality of candidate points, wherein the offset value is a pixel interval between the detected centromere location and the centerline pixel location;
  e) obtaining a fuzzy output result for the two candidate sets;
  f) selecting a maximum result from the two candidate offset sets;
  g) selecting the candidate location with the highest fuzzy logic output for each candidate data set;
  h) calculating a difference between the 2 highest fuzzy logic output values; and
  i) selecting a new centromere location wherein if the difference is greater than 0.1, the centerline pixel with the highest fuzzy logic output is selected as the new centromere location and if the difference is lower than 0.1, the centerline pixel with the lowest offset from the original location is selected as the new centromere location.

18. The method of claim 9 wherein the algorithm using a fuzzy logic system calculates an optimal position for the centromere comprising the steps of:
  (a) defining a search space of the image that includes only a desired centromere location,
  (b) selecting a set of centerline points for the search space based on the desired centromere location,
  (c) drawing a line segment about every 2.5 degrees through each of the selected centerline points,
  (d) determining the endpoints of the line segments using binary object contour,
  (e) determining ResW for each line segment wherein ResW is a ratio of the width of a line segment to an average width of a width profile,
  (f) identifying two line segments with the lowest ResW value, and
  (g) applying an algorithm based on a fuzzy logic system to calculate an optimal position for the centromere from the two line segments with the lowest ResW value.

19. A method of detecting at least one abnormal chromosome of claim 6 further comprising the steps of:
  a) obtaining a thickness profile of each chromosome,
  b) obtaining a width profile of each chromosome,
  c) providing an intensity integrated Laplacian thickness measurement, and
  d) providing a Laplacian operator ($\Delta$) to yield a second order derivative of a chromosome metaphase image to emphasize a chromosome contour, and
  e) detecting a sister chromatid separation using Orthogonal function representation which analyses partitioned contour shapes at a telomere.

20. A computer-implemented method of detecting at least one dicentric chromosome comprising the steps of:
  a) detecting a chromosome that does not overlap another chromosome to obtain a non-overlapping chromosome,
  b) segmenting the non-overlapping chromosome,
  c) determining a centerline for the chromosome,
  d) minimizing a width and an intensity of the chromosome,
  e) detecting a centromere,
  f) detecting a second centromere location by masking the neighborhood of the first centromere location and then finding the global minima of width and intensity,
  g) detecting sister chromatid separation, whereby a centromere refinement method is used if the sister chromatid separation is detected, and
  h) detecting a second centromere.

21. The computer-implemented method of claim 20, wherein the centromere refinement method is used to process images of metaphase chromosomes prepared by culturing cells with either high concentrations or extended duration exposure to a microtubule inhibitory compound.

22. The computer-implemented method of claim 20, wherein the centromere refinement method is used to process images of metaphase chromosomes prepared by culturing cells with either low concentrations or shorter duration exposure to a microtubule inhibitory compound.

23. A method of detecting at least one abnormal chromosome of claim 6 or 19 further comprising the steps of:
  producing image data of centromeres to be recognized by fuzzy logic system application;
  inputting said image data into a learning vector quantization network to produce optimized moment invariant vectors associated with each of said fuzzy logic system;
  accessing an algorithm to produce a plurality of candidate chromosome centerlines representing said parameters for said fuzzy logic system;
  transforming each of said plurality of candidate chromosome centerlines into said parameters for said fuzzy logic system;
  importing said parameters into said fuzzy logic system for said each of said plurality of candidate chromosome centerlines;
  simulating said fuzzy logic system with respect to said each of said plurality of candidate chromosome centerlines;
  inputting said optimized moment invariant vectors into said fuzzy logic system;
  with respect to said each of said plurality of candidate chromosome centerlines, determining how many of said centromeres are correctly recognized by said fuzzy logic system;
  selecting one of said plurality of candidate chromosome centerlines if said one of said plurality of candidate chromosome centerlines correctly recognizes all of said centromeres;
  associating a score with said each of said plurality of candidate chromosome centerlines, said score indicating how many of said centromeres were recognized by said each of said plurality of candidate chromosome centerlines;

selecting a percentage of said plurality of candidate chromosome centerlines having better scores;

applying a crossover process between said selected percentage of said plurality of candidate chromosome centerlines to produce one or more children;

replacing one or more of said plurality of said candidate chromosome centerlines having worst scores with said one or more children, resulting in a new population of candidate chromosome centerline;

transforming said new population into fuzzy logic parameters;

importing said fuzzy logic parameters of said new population into said fuzzy logic system;

simulating said fuzzy logic system with respect to said new population;

inputting said optimized moment invariant vectors into said fuzzy logic system;

with respect to each of said plurality of candidate chromosome centerlines in said new population, determining how many of said centromeres are correctly recognized by said fuzzy logic system; and selecting one of said plurality of candidate chromosome centerlines in said new population if said one of said plurality of candidate chromosome centerlines in said new population correctly recognizes all of said centromeres.

24. The method as recited in claim 23, wherein said rules comprise:

If ResW is very low and ResDA is low, then output level is ultra high,

If ResW is very low and ResDA is medium, then output level is ultra high,

If ResW is low and ResDA is low, then output level is very high,

If ResW is low and ResDA is medium, then output level is medium high,

If ResW is low and ResDA is high, then output level is medium low,

If ResW is medium and ResDA is low and ResInt is high then output level is medium high, If ResW is medium and ResDA is medium and ResInt is high then output level is medium low, If ResW is medium and ResDA is high, then output level is very low, If ResW is medium and ResDA is low and ResInt is low then output level is medium low, If ResW is medium and ResDA is medium and ResInt is low then output level is very low, and If ResW is high then output level is ultra low;

wherein ResW is a ratio of the width of a line segment to an average width of a width profile, ResDA is an angular difference between a direction of a line segment and an expected direction given by a line perpendicular to P1-P3 through P2, wherein P1, P2 and P3 are any 3 consecutive points on a pruned chromosome centerline and ResInt is an average pixel intensity in a 5 pixel region surrounding a candidate centerline pixel wherein said average pixel intensity value is normalized by a ratio of average pixel intensity local neighborhood to maximum average intensity in a search space.

25. At least one non-transitory computer readable medium that stores a set of instructions for running on a computer system, comprising:

a. instructions for receiving one or more electronic files of images into one or more memory;

b. instructions for identifying image content resembling a metaphase nucleus containing discrete, adjacent chromosomes;

c. instructions for identifying metaphase chromosomes and portions thereof in the image content;

d. instructions for determining local classification parameters of metaphase chromosomes and chromosomes connected to neighboring chromosomes;

e. instructions for extracting chromosome features from the image content;

f. instructions for applying a classification system based on extracted chromosome features to the image content to separate a plurality of different categories of images, the categories consisting of a nice classification, an overlapped classification, and an overspread classification, wherein a nice classification is an image having at least one chromosome that is fully contained in the image and having substantially no overlap with another chromosome, an overlapped classification is an image having at least two chromosomes that are superimposed on one another, and an overspread classification is an image having at least one chromosome that is only partially contained in the image sector;

g. instructions for applying a ranking system to the images based upon a plurality of global parameters;

h. instructions for selecting a subset of images based upon rank;

i. instructions for determining contours of the chromosome;

j. instructions for determining the location of the centerline of the chromosome;

k. instructions for locating the most likely position of at least one centromere in the chromosome, whereby a plurality of chromosomes in the same cell are classified based on position;

l. instructions for measuring a centromere confidence value to measure the probable location of the automated centromere detection process;

m. instructions for masking the most likely location for the first centromere and recomputing the centromere confidence value to determine if subsequent centromeres are present on the same chromosome n. instructions for counting the number of centromeres in the chromosome;

o. instructions for computing a frequency of dicentric chromosomes in at least one cell; and p. instructions for determining a radiation dose by comparing the computed frequency of each dicentric chromosome with a previously determined dose-response curve from a calibrated source.

26. The set of instructions stored on the at least one non-transitory computer readable medium of claim 25, wherein the instructions a.-p. are adapted to be executed without manual intervention.

27. The set of instructions stored on the at least one non-transitory computer readable medium of claim 25, further comprising at least one instruction for storing information indicative of the content resembling a metaphase chromosome.

28. The set of instructions stored on the at least one non-transitory computer readable medium of claim 25, further comprising at least one instruction for storing information for determining local classification parameters of metaphase chromosomes and chromosomes connected to neighboring chromosomes.

29. The set of instructions stored on the at least one non-transitory computer readable medium of claim 25, further comprising at least one instruction for storing global ranking parameters of metaphase chromosomes and chromosomes connected to neighboring chromosomes.

30. The set of instructions stored on the at least one non-transitory computer readable medium of claim 25, further comprising at least one instruction for storing the ranked images.

31. The set of instructions stored on the at least one non-transitory computer readable medium of claim 25, further comprising at least one instruction for storing contours of chromosomes.

32. The set of instructions stored on the at least one non-transitory computer readable medium of claim 25, further comprising at least one instruction for storing the location of the centerline of metaphase chromosomes.

33. The set of instructions stored on the at least one non-transitory computer readable medium of claim 25, further comprising at least one instruction for storing the number of centromeres in a metaphase chromosome.

34. The set of instructions stored on the at least one non-transitory computer readable medium of claim 25, further comprising at least one instruction for storing the location of centromeres in a metaphase chromosome.

35. The set of instructions stored on the at least one non-transitory computer readable medium of claim 25, further comprising at least one instruction for storing a determination of an abnormal chromosome.

36. The set of instructions stored on the at least one non-transitory computer readable medium of claim 25, where the instructions are adapted to determining the frequency of dicentric chromosomes in a set of images of metaphase nuclei.

37. The set of instructions stored on the at least one non-transitory computer readable medium of claim 25, where the instructions are adapted to determining the centromere confidence value to determine the most probable locations of one or more centromeres in a chromosome.

38. The set of instructions stored on the at least one non-transitory computer readable medium of claim 25, where the instructions are adapted to determining a radiation dose by comparing the computed frequency of each dicentric chromosome with a previously determined dose-response curve from a calibrated source.

* * * * *